United States Patent
Kubota et al.

(10) Patent No.: US 7,504,526 B2
(45) Date of Patent: Mar. 17, 2009

(54) ANTHRACENE DERIVATIVE AND ORGANIC ELECTROLUMINESCENCE DEVICE EMPLOYING THE SAME

(75) Inventors: Mineyuki Kubota, Chiba (JP);
Masakazu Funahashi, Chiba (JP);
Chishio Hosokawa, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 11/282,818

(22) Filed: Nov. 21, 2005

(65) Prior Publication Data

US 2006/0154076 A1 Jul. 13, 2006

Related U.S. Application Data

(63) Continuation of application No. PCT/JP2005/009168, filed on May 19, 2005.

(30) Foreign Application Priority Data

Jun. 9, 2004 (JP) .............................. 2004-171660

(51) Int. Cl.
*C07C 49/675* (2006.01)
*B32B 9/04* (2006.01)
*H01J 1/62* (2006.01)

(52) U.S. Cl. .................... 552/218; 428/411.1; 428/690; 428/917; 313/504; 313/506

(58) Field of Classification Search .................. 257/40, 257/100; 428/917, 690, 411.1; 313/504, 313/506; 564/433, 434, 429; 548/440; 552/218
See application file for complete search history.

(56) References Cited

U.S. PATENT DOCUMENTS 5,811,834 A * 9/1998 Tamano et al. ................ 257/40
2002/0048687 A1 4/2002 Hosokawa et al.
2004/0100188 A1 5/2004 Hosokawa et al.
2005/0089717 A1 * 4/2005 Cosimbescu et al. ........ 428/690

FOREIGN PATENT DOCUMENTS

| EP | 1 541 657 A1 | 6/2005 |
| EP | 1 553 154 A1 | 7/2005 |
| EP | 1 707 550 A1 | 10/2006 |
| EP | 1 750 488 A1 | 2/2007 |
| JP | 3-200889 | 9/1991 |
| JP | 7-138561 | 5/1995 |
| JP | 8-12600 | 1/1996 |
| JP | 8-239655 | 9/1996 |
| JP | 2000-182776 | 6/2000 |
| JP | 2001-257074 | 9/2001 |
| JP | 2004-59535 | 2/2004 |
| WO | WO 2004/018587 A1 | 3/2004 |

OTHER PUBLICATIONS

U.S. Appl. No. 10/572,586, filed Mar. 20, 2006, Kubota, et al.
U.S. Appl. No. 11/282,818, filed Nov. 21, 2005, Kubota, et al.
C. W. Tang, et al., "Organic Electroluminescent Diodes", Appl. Phys. Lett., vol. 51, No. 12, Sep. 21, 1987, pp. 913-915.

* cited by examiner

*Primary Examiner*—D. Lawrence Tarazano
*Assistant Examiner*—Camie S Thompson
(74) *Attorney, Agent, or Firm*—Oblon, Spivak, McClelland, Maier & Neustadt, P.C.

(57) ABSTRACT

An anthracene derivative with a specified asymmetrical type structure. An organic electroluminescence device which comprises at least one organic thin film layer including a light emitting layer sandwiched between a pair of electrode consisting of an anode and a cathode, wherein at least one of the organic thin film layer comprises the anthracene derivative. An organic electroluminescence device which emits blue light of enhanced purity and has a long lifetime is provided.

10 Claims, No Drawings

ANTHRACENE DERIVATIVE AND ORGANIC ELECTROLUMINESCENCE DEVICE EMPLOYING THE SAME

TECHNICAL FIELD

The present invention relates to an organic electroluminescence device and an anthracene derivative, and more particularly, the present invention relates to the organic electroluminescence device emitting highly pure light with long lifetime, together with the anthracene derivative realizing the organic electroluminescence device.

BACKGROUND ART

An organic electroluminescence ("electroluminescence" will be occasionally referred to as "EL", hereinafter) device is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported by C. W. Tang et al. of Eastman Kodak Company (C. W. Tang and S. A. Vanslyke, Applied Physics Letters, Volume 51, Pages 913, 1987), many studies have been conducted on organic EL devices using organic materials as the constituting materials. Tang et al. used a laminate structure using tris(8-hydroxyquinolinol aluminum) for the light emitting layer and a triphenyldiamine derivative for the hole transporting layer. Advantages of the laminate structure are that the efficiency of hole injection into the light emitting layer can be increased, that the efficiency of forming excited particles which are formed by blocking and recombining electrons injected from the cathode can be increased, and that excited particles formed among the light emitting layer can be enclosed. As the structure of the organic EL device, a two-layered structure having a hole transporting (injecting) layer and an electron transporting and light emitting layer and a three-layered structure having a hole transporting (injecting) layer, a light emitting layer and an electron transporting (injecting) layer are well known. To increase the efficiency of recombination of injected holes and electrons in the devices of the laminate type, the structure of the device and the process for forming the device have been studied.

As the light emitting material of the organic EL device, chelate complexes such as tris(8-quinolinolato)aluminum, coumarine derivatives, tetraphenylbutadiene derivatives, bis-styrylarylene derivatives and oxadiazole derivatives are known. It is reported that light in the visible region ranging from blue light to red light can be obtained by using these light emitting materials, and development of a device exhibiting color images is expected (refer to, for example, Patent Literatures 1 to 3 below).

A device using a phenylanthracene derivative as the light emitting material is disclosed in Patent Literature 4 below. Although the anthracene derivative is used as the material for emitting blue light, a further improvement in the lifetime extension has been desired. Further, an anthracene material having a fluoranthene group at 9, 10 positions for the EL device is disclosed in Patent Literature 5 below. Although the anthracene derivative was also used as a material for emitting blue light, improvement of lifetime was still required. Furthermore, Patent Literature 6 below discloses that various kinds of anthracene derivatives are employed as a hole transporting material. However, synthesis of the anthracene derivatives were neither tried yet and accordingly, the evaluation regarding luminescent material was nor achieved yet.

Still further, Patent Literature 7 below discloses an asymmetry type anthracene derivative, however, a compound enabling to emit highly pure blue light was eagerly demanded.

Patent Literature 1: Japanese Patent Application Laid-Open No. Heisei 8(1996)-239655
Patent Literature 2: Japanese Patent Application Laid-Open No. Heisei 7(1995)-138561
Patent Literature 3: Japanese Patent Application Laid-Open No. Heisei 3(1991)-200289
Patent Literature 4: Japanese Patent Application Laid-Open No. Heisei 8(1996)-012600
Patent Literature 5: Japanese Patent Application Laid-Open No. 2001-257074
Patent Literature 6: Japanese Patent Application Laid-Open No. 2000-182776
Patent Literature 7: International PCT Publication No. WO 04/018587

DISCLOSURE OF THE INVENTION

The present invention has been made to overcome the above problems and has an object of providing an organic EL device which emits blue light with high purity and of long lifetime, and an object of providing an anthracene derivative realizing the EL device.

As a result of intensive researches and studies to achieve the above object by the present inventors, it was found that an employment of an anthracene compound having a specified asymmetric structure represented by a following general formula (I) as a material for the organic EL device provides the EL device with long lifetime, resultantly completing the present invention.

Namely, the present invention provides an anthracene derivative represented by a following general formula (I):

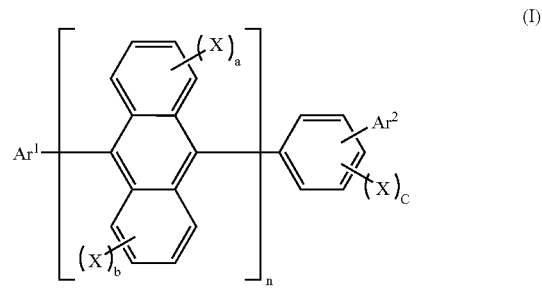

In the general formula (I), X represents a hydrogen atom, a substituted or unsubstituted aromatic group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group having 1 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 2 to 50 carbon atoms, a substituted or unsubstituted silyl group, a carboxyl group, a halogen atom, a cyano group, a nitro group or a hydroxyl group.

$Ar^1$ and $Ar^2$ each independently represents a substituted or unsubstituted condensed aromatic group having 10 to 50 ring carbon atoms; at least one of $Ar^1$ or $Ar^2$ represents a 1-naphthyl group represented by a following general formula (II), a 2-naphthyl group represented by a following general formula (III) or a triptycenyl group represented by a following general formula (IV).

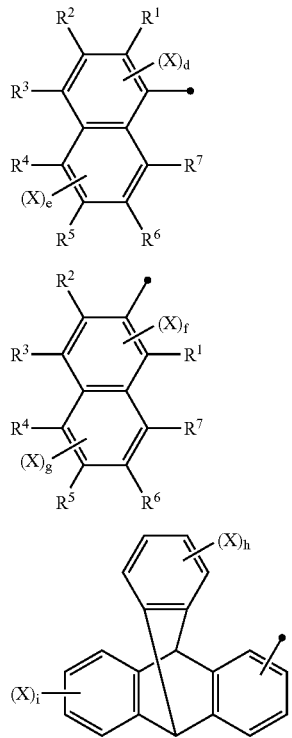

In the general formulae (II) to (IV), $R^1$ to $R^7$ each independently represents a hydrogen atom, a substituted or unsubstituted alkyl group having 1 to 50 carbon atoms; at least one adjacent couple among $R^1$ to $R^7$ are equally alkyl groups bonding each other to form a ring structure. X represents the same as the foregoing description; d,e,f,g,h and i each independently represents an integer of 0 to 4;

a, b and c each independently represents an integer of 0 to 4;

n represents an integer of 1 to 3; and when n is 2 or greater,

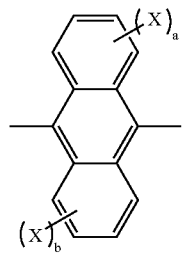

within the parentheses: [ ] in the general formula (I) may be the same with or different from each other.

Further, the present invention provides an organic electroluminescence device which comprises at least one organic thin film layer including a light emitting layer sandwiched between a pair of electrode consisting of an anode and a cathode, wherein at least one of the organic thin film layer comprises the anthracene derivative singly or as its mixture component.

Both the organic EL device of the present invention and the organic EL device employing the anthracene derivative of the present invention emit blue light of enhanced purity and have a long lifetime.

THE PREFERRED EMBODIMENT TO CARRY OUT THE INVENTION

The anthracene derivative of the present invention is represented by a following general formula (I):

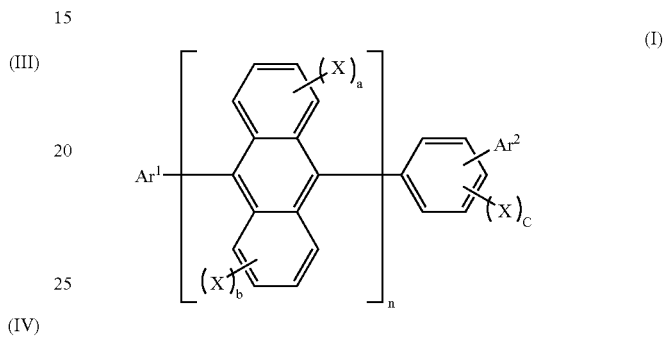

In the general formula (I), X represents a hydrogen atom, a substituted or unsubstituted aromatic group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 1 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 2 to 50 carbon atoms, a substituted or unsubstituted silyl group, a carboxyl group, a halogen atom, a cyano group, a nitro group or a hydroxyl group.

Examples of the aromatic group represented by X include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl) phenyl group, 3-methyl-2-naphthyl group, 4-methyl-1-naphthyl group, 4-methyl-1-anthryl group, 4'-methylbiphenyl-yl group, 4"-t-butyl-p-terphenyl-4-yl group, etc.

Examples of the aromatic heterocyclic group represented by X include 1-pyrrolyl group, 2-pyrrolyl group, 3-pyrrolyl group, pyradinyl group, pyrimidyl group, pyridazyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl 1-indolyl group, 4-t-butyl 1-indolyl group, 2-t-butyl 3-indolyl group, 4-t-butyl 3-indolyl group, etc.

Examples of the alkyl group represented by X include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxy-isopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triamino-propyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyano-propyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, etc.

Examples of the cycloalkyl group represented by X include cyclopropyl group, cyclobutyl group, cyclopentyl group, cyclohexyl group, 4-methylcyclohexyl group, 1-adamanthyl group, 2-adamanthyl group, 1-norbornyl group, 2-norbornyl group, etc.

The alkoxy group represented by X is a group expressed as —OY, and examples include the same examples described as the foregoing examples of alkyl group.

Examples of the aralkyl group represented by X include benzyl group, 1-phenylethyl group, 2-phenylethyl group, 1-phenyl-isopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, 1-chloro-2-phenylisopropyl group, etc.

The aryloxy group represented by X is a group expressed as —OY. Examples of the group represented by Y' include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-pyrrolyl group, 3-pyrrolyl group, pyradinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methyl-pyrrol-5-yl group, 3-methylpyrrol-1-yl group, 3-methyl-pyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group, etc.

The arylthio group represented by X is a group expressed as —SY". Examples of the group represented by Y" include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-pyrrolyl group, 3-pyrrolyl group, pyradinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 2-phenothiazinyl group, 2-phenothiazinyl group, 3-phenothiazinyl group, 4-phenothiazinyl group, 2-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methyl-pyrrol-5-yl group, 3-methylpyrrol-1-yl group, 3-methyl-pyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group, etc.

The alkoxycarbonyl group represented by X is a group expressed as —COOZ, and examples of Z include the same examples described as the foregoing examples of the alkyl group.

Examples of the halogen atom represented by X include fluorine atom, chlorine atom, bromine atom, iodine atom, etc.

In the general formula (I), $Ar^1$ and $Ar^2$ each independently represents a substituted or unsubstituted condensed aromatic group having 10 to 50 ring carbon atoms.

Examples of the condensed aromatic group represented by $Ar^1$ or $Ar^2$ include 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 3-methyl-2-naphthyl group, 4-methyl-1-naphthyl group, 4-methyl-1-anthryl group, etc.

However, in the anthracene derivative of the present invention, at least one of $Ar^1$ or $Ar^2$ represents a 1-naphthyl group represented by a following general formula (II), a 2-naphthyl group represented by a following general formula (III) or a triptycenyl group represented by a following general formula (IV):

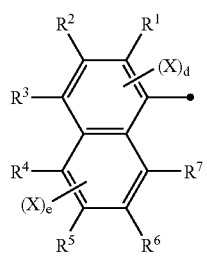
(II)

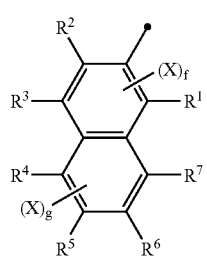
(III)

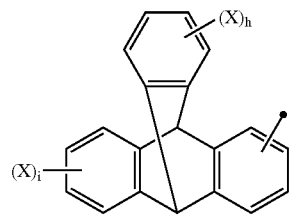
(IV)

In the general formulae (II) and (III), $R^1$ to $R^7$ each independently represents a hydrogen atom, a substituted or unsubstituted alkyl group having 1 to 50 carbon atoms; at least one adjacent couple among $R^1$ to $R^7$ are equally alkyl groups bonding each other to form a ring structure.

Examples of the alkyl group represented by $R^1$ to $R^7$ include the same examples described as the foregoing examples of the alkyl group represented by X.

Examples of the ring structure formed by the adjacent group among $R^1$ to $R^7$ include cycloalkanes such as cyclopropane, cyclobutane, cyclopentane, cyclohexane, cycloheptane, cyclooctane and so on; or cycloalkenes such as cyclobutene, cyclopentene, cyclohexene, cycloheptene, cyclo octene and so on; while cyclopentane, cyclohexane, cyclopentene and cyclohexene are preferable.

Further, the ring structure may be further substituted. Examples of the substituent include oxygen atom, sulfur atom, substituted or unsubstituted aromatic group having 6 to 50 ring carbon atoms, substituted or unsubstituted aromatic heterocyclic group having 5 to 50 ring atoms, substituted or unsubstituted alkyl group having 1 to 50 carbon atoms, substituted or unsubstituted alkoxy group having 1 to 50 carbon atoms, substituted or unsubstituted aralkyl group having 6 to 50 carbon atoms, substituted or unsubstituted aryloxy group having 5 to 50 ring atoms, substituted or unsubstituted arylthio group having 5 to 50 ring atoms, substituted or unsubstituted alkoxycarbonyl group having 1 to 50 carbon atoms, carboxyl group, halogen atom, cyano group, nitro group or hydroxyl group. Specific examples are the same as those explained about the foregoing X.

Specific examples of the ring structure formed by the adjacent group among $R^1$ to $R^7$ in the general formulae (II) and (III) are as the following:

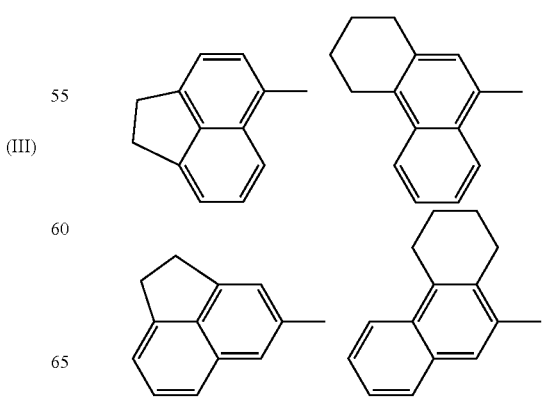

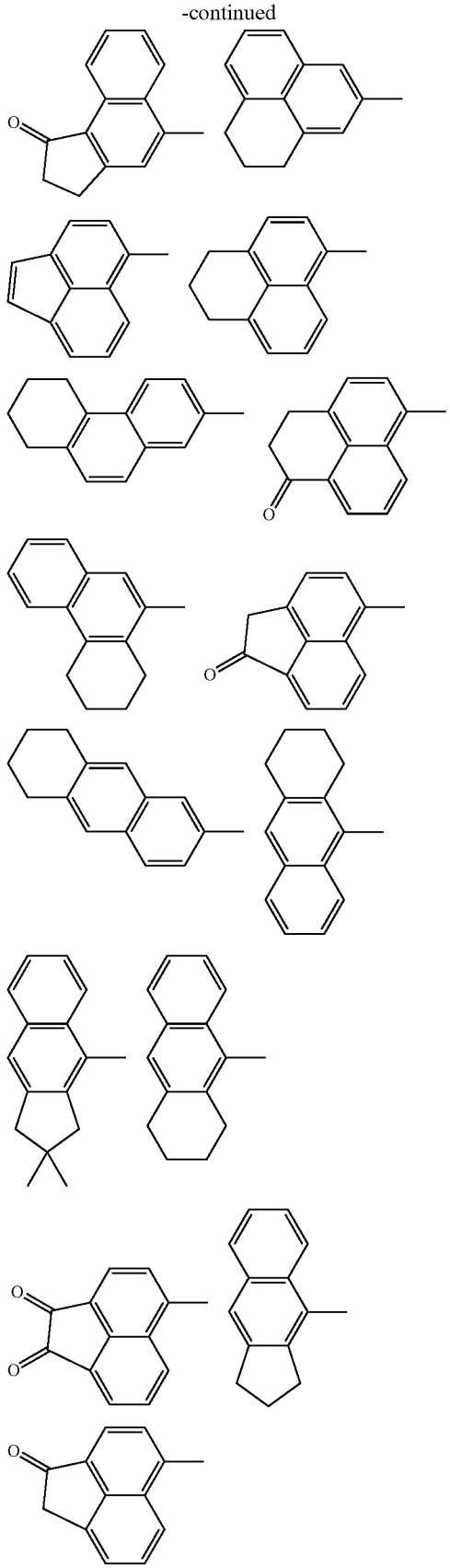

On the other hand, examples of the adjacent group among $R^1$ to $R^7$ in the general formulae (II) and (III) not forming a ring structure include 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 3-methyl-2-naphthyl group, 4-methyl-1-naphthyl group, 4-methyl-1-anthryl group, etc.

In the general formulae (II) to (IV), d, e, f, g, h and i each independently represents an integer of 0 to 4, preferably 0 or 1.

In the general formulae (II) to (IV), X represents the same as the foregoing description including the examples.

In the general formula (I), a, b and c each represents an integer of 1 to 3, preferably 0 or 1.

n represents an integer of 1 to 3. When n is 2 or greater, groups within the parentheses: [ ] may be the same with or different from each other.

Examples of the substituent of the group represented by the foregoing $Ar^1$, $Ar^2$ and X include substituted or unsubstituted aromatic group having 6 to 50 ring carbon atoms, substituted or unsubstituted aromatic heterocyclic group having 5 to 50 ring atoms, substituted or unsubstituted alkyl group having 1 to 50 carbon atoms, substituted or unsubstituted cycloalkyl group having 1 to 50 carbon atoms, substituted or unsubstituted alkoxy group having 1 to 50 carbon atoms, substituted or unsubstituted aralkyl group having 6 to 50 carbon atoms, substituted or unsubstituted aryloxy group having 5 to 50 ring atoms, substituted or unsubstituted arylthio group having 5 to 50 ring atoms, substituted or unsubstituted alkoxycarbonyl group having 1 to 50 carbon atoms, substituted or unsubstituted silyl group, carboxyl group, halogen atom, cyano group, nitro group or hydroxyl group. Specific examples are the same as those explained about the foregoing X.

Specific examples of the anthracene derivative represented by the general formula (1) of the present invention include the following compounds, though not limited thereto.

AN-1

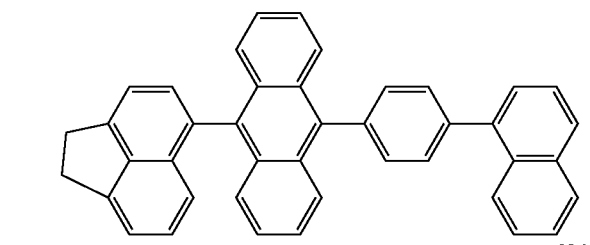

AN-2

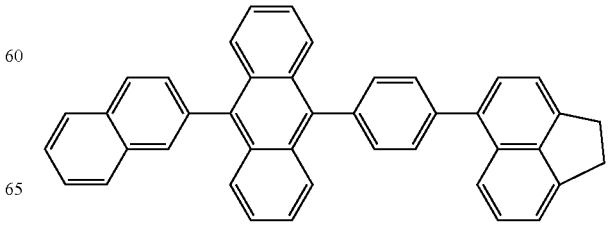

-continued
AN-3
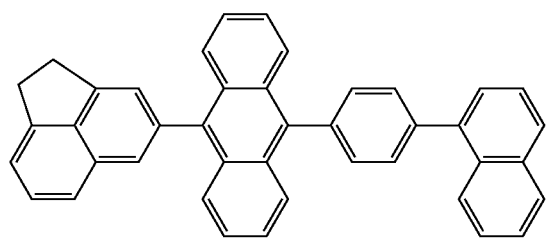
AN-4
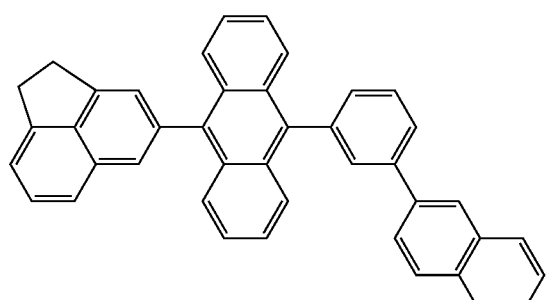
AN-5
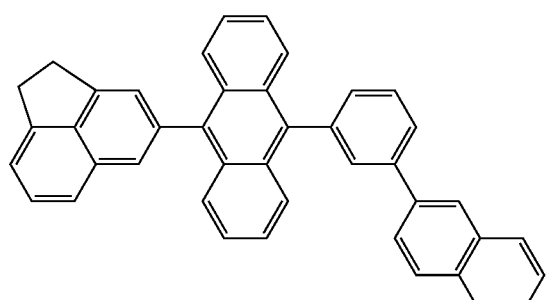
AN-6
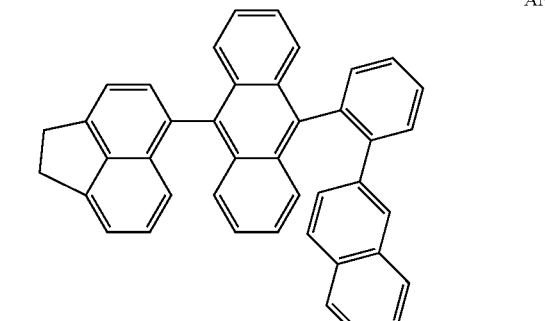
AN-7
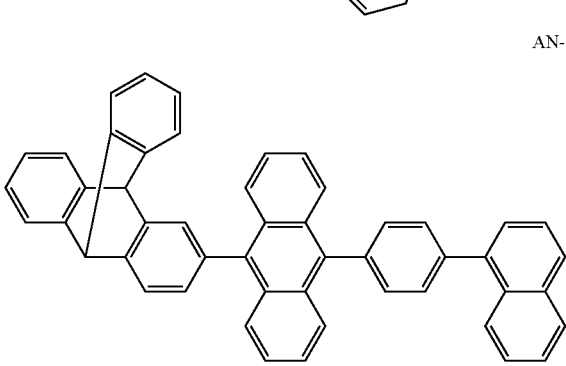
-continued
AN-8
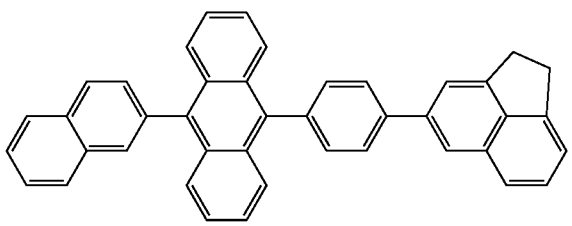
AN-9
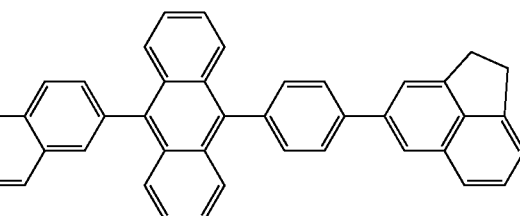
AN-10
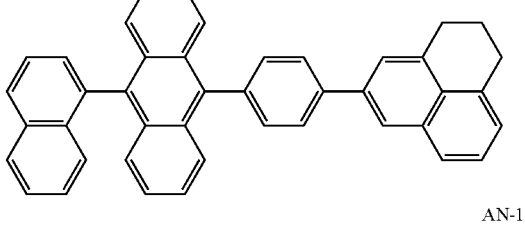
AN-11
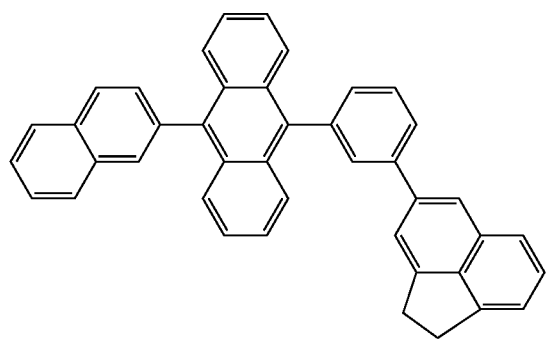
AN-12
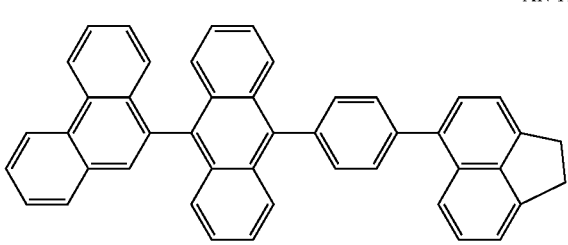
AN-13
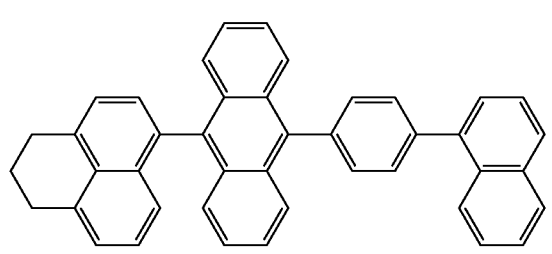

-continued
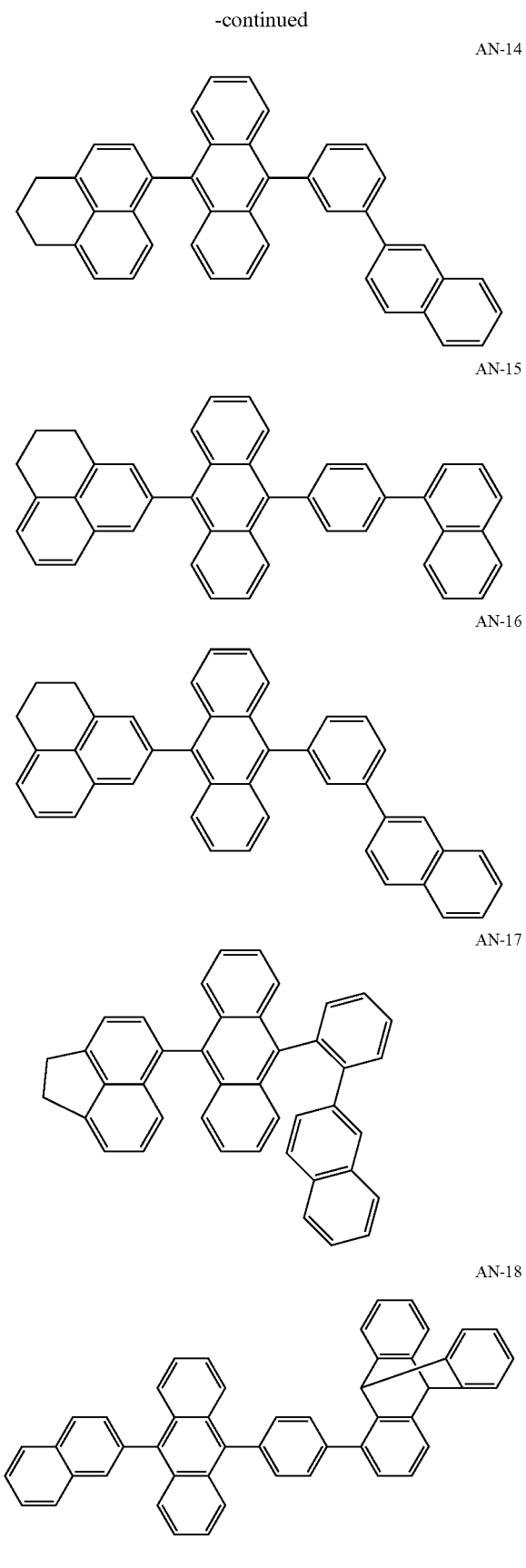
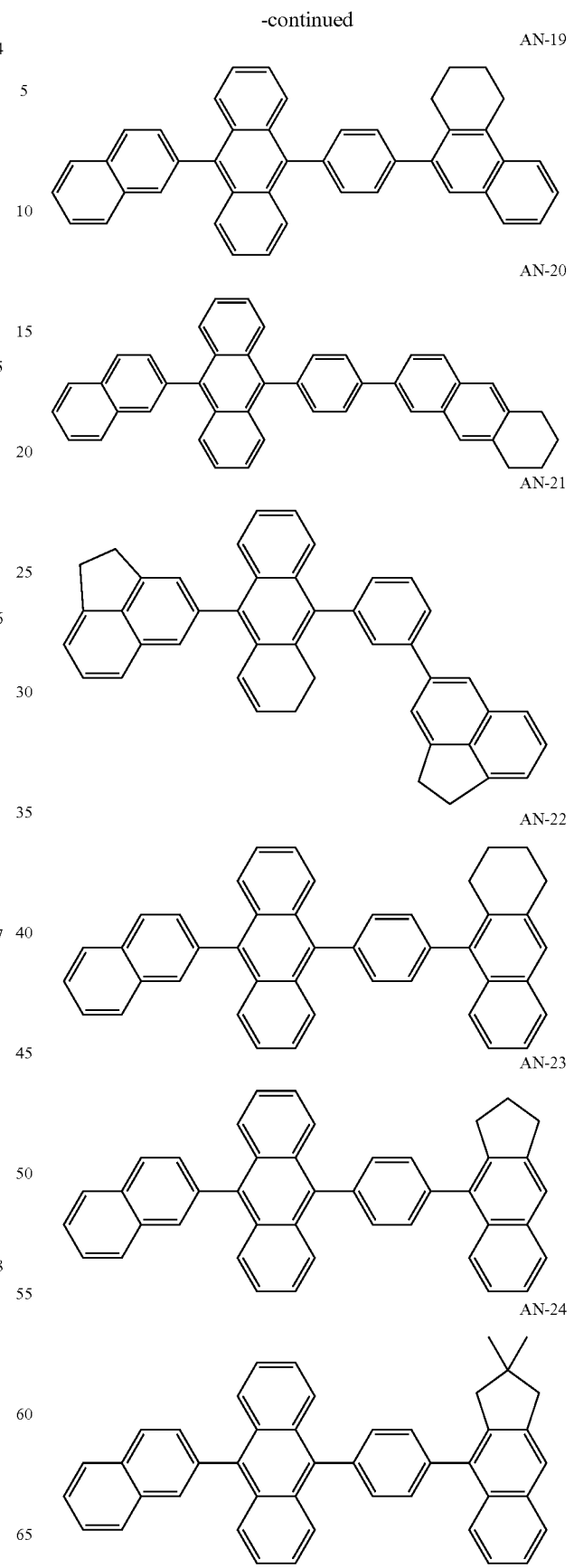

-continued
AN-25
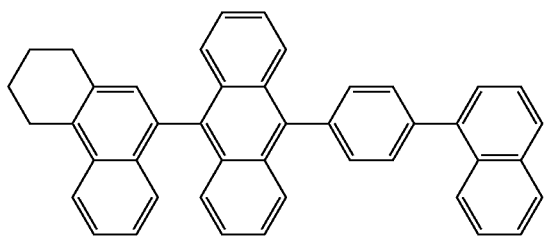
AN-26
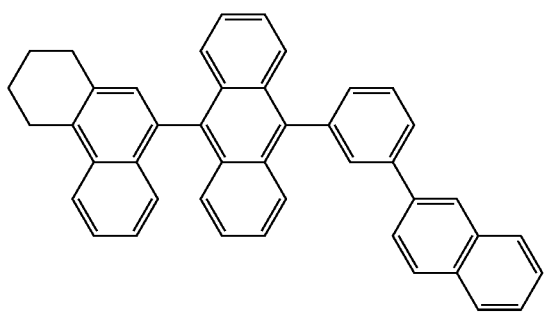
AN-27
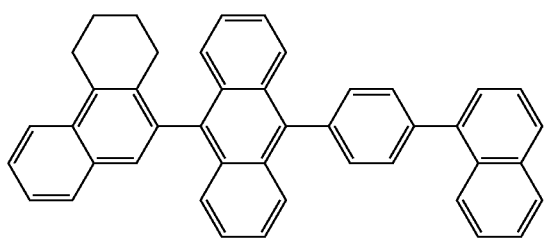
AN-28
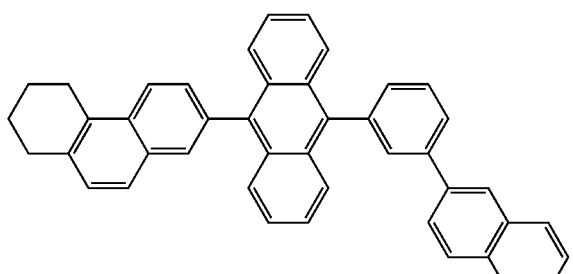
AN-29
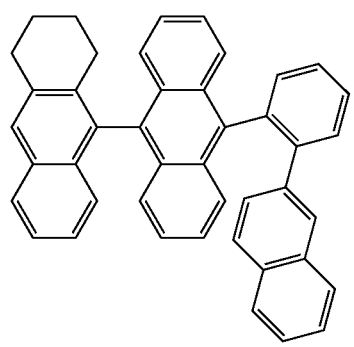
-continued
AN-30
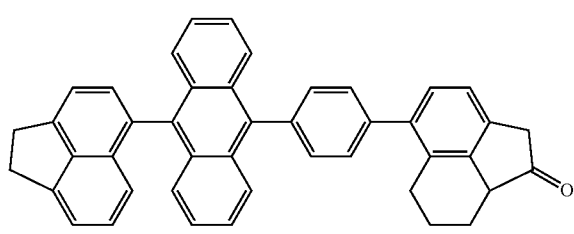
AN-31
AN-32
AN-33
AN-34
AN-35
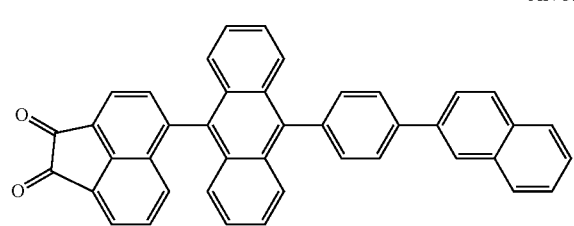

-continued

AN-36

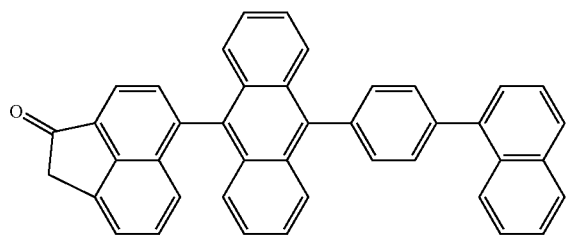

AN-37

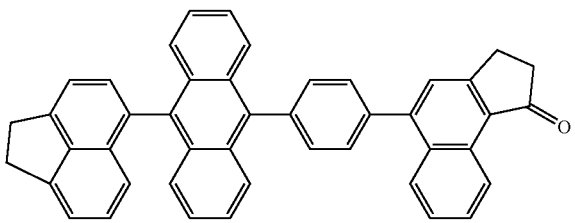

AN-38

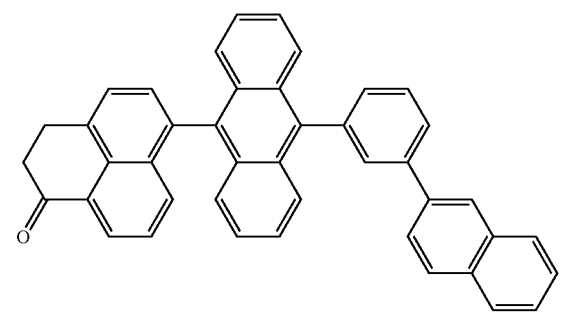

AN-39

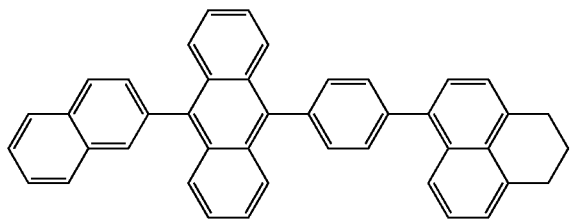

Further, the present invention provides an organic electroluminescence device which comprises at least one organic thin film layer including a light emitting layer sandwiched between a pair of electrode consisting of an anode and a cathode, wherein at least one of the organic thin film layer comprises the anthracene derivative represented by the general formula (I) singly or as its mixture component.

It is preferable for the organic EL device of the present invention that the light emitting layer comprises the anthracene derivative represented by the general formula (I) as an essential component Moreover, it is preferable for the organic EL device of the present invention that the light emitting layer further comprises an arylamine compound and/or a styrylamine compound.

With regard to the styrylamine compound, a compound represented by a following general formula (A):

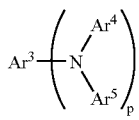

(A)

is preferable.

In the general formula (A), $Ar^3$ represents a group selected from phenyl group, biphenyl group, terphenyl group, stilbene group and distyrylaryl group; $Ar^4$ and $Ar^5$ each independently represents a hydrogen atom or a aromatic group having 2 to 20 carbon atoms; and $Ar^3$ to $Ar^5$ may be independently substituted; p represents an integer of 1 to 4; and at least one of $Ar^4$ or $Ar^5$ is further preferably substituted with a styryl group.

Examples of the aromatic group having 2 to 20 carbon atoms include phenyl group, naphthyl group, anthranil group, phenanthryl group, terphenyl group, etc.

With regard to the arylamine compound, a compound represented by a following general formula (B):

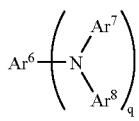

(B)

is preferable.

In the general formula (B), $Ar^6$ to $Ar^8$ each independently represents substituted or unsubstituted aryl group having 5 to 40 ring carbon atoms; and q represents an integer of 1 to 4.

Examples of the aryl group having 5 to 40 ring carbon atoms include phenyl group, naphthyl group, anthranil group, phenanthryl group, pyrenyl group, coronyl group, biphenyl group, terphenyl group, pyrrolyl group, furanyl group, thiophenyl group, benzthiophenyl group, oxadiazolyl group, diphenylanthranil group, indolyl group, carbazolyl group, pyridyl group, benzquinolyl group, fluoranthenyl group, acenaphthofluoranthenyl group, stilbene group, perilenyl group, chrysenyl group, picenyl group, triphenylenyl group, rubicenyl group, benzanthracenyl group, phenyl anthranil group, bisanthracenyl group, or aryl group represented by following general formulae (C) and (D); preferably naphthyl group, anthranil group, chrysenyl group, pyrenyl group, or aryl group represented by the following general formula (D).

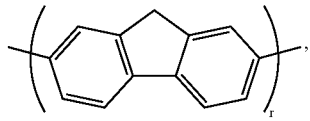

(C)

-continued

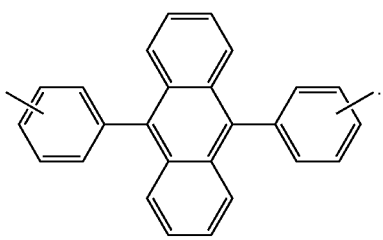
(D)

In the general formula (C), r represents an integer of 1 to 3.

Additionally, examples of the preferable substituent for the aryl group include alkyl group having 1 to 6 carbon atoms (ethyl group, methyl group, i-propyl group, n-propyl group, s-butyl group, t-butyl group, pentyl group, hexyl group, cyclopentyl group, cyclohexyl group, etc.), alkoxy group having 1 to 6 carbon atoms (ethoxy group, methoxy group, i-propoxy group, n-propoxy group, s-butoxy group, t-butoxy group, pentoxy group, hexyloxy group, cyclopentoxy group, cyclohexyloxy group, etc.), aryl group having 5 to 40 ring carbon atoms, amino group substituted with aryl group having 5 to 40 ring carbon atoms, ester group possessing aryl group having 5 to 40 ring carbon atoms, ester group possessing alkyl group having 1 to 6 carbon atoms, cyano group, nitro group, halogen atom, etc.

The construction of the organic EL device of the present invention will be explained below.

Typical examples of the construction of the organic EL device of the present invention include:

(1) An anode/a light emitting layer/a cathode;
(2) An anode/a hole injecting layer/a light emitting layer/a cathode;
(3) An anode/a light emitting layer/an electron injecting layer/a cathode;
(4) An anode/a hole injecting layer/a light emitting layer/an electron injecting layer/a cathode;
(5) An anode/an organic semiconductor layer/a light emitting layer/a cathode;
(6) An anode/an organic semiconductor layer/an electron barrier layer/a light emitting layer/a cathode;
(7) An anode/an organic semiconductor layer/a light emitting layer/an adhesion improving layer/a cathode;
(8) An anode/a hole injecting layer/a hole transporting layer/a light emitting layer/an electron injecting layer/a cathode;
(9) An anode/an insulating layer/a light emitting layer/an insulating layer/a cathode;
(10) An anode/an inorganic semiconductor layer/an insulating layer/a light emitting layer/an insulating layer/a cathode;
(11) An anode/an organic semiconductor layer/an insulating layer/a light emitting layer/an insulating layer/a cathode;
(12) An anode/an insulating layer/a hole injecting layer/a hole transporting layer/a light emitting layer/an insulating layer/a cathode; and
(13) An anode/an insulating layer/a hole injecting layer/a hole transporting layer/a light emitting layer/an electron injecting layer/a cathode.

Among those, the construction of above item (8) is preferably employed. However, the construction of the organic EL device is not limited to those shown above as the examples.

Further, in the organic EL device of the present invention, the anthracene derivative of the present invention may be used for any of the above-mentioned organic layer, however, it is preferable for the anthracene derivative to be contained in the light emitting zone or in the hole transporting zone among the above construction components and that the amount to be contained is selected from among 30 to 100% by mol.

In general, the organic EL device is fabricated on a substrate which transmits light. It is preferable that the substrate which transmits light has a transmittance of light of 50% or greater in the visible region of 400 to 700 nm. It is also preferable that a flat and smooth substrate is employed.

As the substrate which transmits light, for example, glass sheet and synthetic resin sheet are advantageously employed. Specific examples of the glass sheet include soda ash glass, glass containing barium and strontium, lead glass, aluminosilicate glass, borosilicate glass, barium borosilicate glass and quartz. Specific examples of the synthetic resin sheet include sheet made of polycarbonate resins, acrylic resins, polyethylene terephthalate resins, polyether sulfide resins and polysulfone resins.

The anode in the organic EL device of the present invention covers a role of injecting holes into a hole transport layer or into a light emitting layer, and it is effective that the anode has a work function of 4.5 eV or greater. Specific examples of the material for the anode include indium tin oxide alloy (ITO), tin oxide (NESA), gold, silver, platinum, copper, etc. With regard to the cathode, its material preferably has a small work function with the aim of injecting electrons into an electron transport layer or into a light emitting layer.

The anode can be prepared by forming a thin film of the electrode material described above in accordance with a process such as a vapor deposition process or a sputtering process.

When the light emitted from the light emitting layer is observed through the anode, it is preferable that the anode has a transmittance of the emitted light greater than 10%. It is also preferable that the sheet resistivity of the anode is several hundred $\Omega/\square$ or smaller. The thickness of the anode is, in general, selected in the range of from 10 nm to 1 μm and preferably in the range of from 10 to 200 nm.

In the organic EL device of the present invention, the light emitting layer has the following functions:

(1) The injecting function: the function of injecting holes from the anode or the hole injecting layer and injecting electrons from the cathode or the electron injecting layer when an electric field is applied;

(2) The transporting function: the function of transporting injected charges (electrons and holes) by the force of the electric field; and (3) The light emitting function: the function of providing the field for recombination of electrons and holes and leading the recombination to the emission of light.

As the process for forming the light emitting layer, a well known process such as the vapor deposition process, the spin coating process and the Langmuir-Blodgett (LB) process can be employed. It is particularly preferable for the light emitting layer to be a molecular sedimentation film. The molecular sedimentation film is defined as a film formed from a material compound in gas phase condition by its sedimentation, or a film formed from a material compound in a solution condition or a liquid phase condition by its condensation. Usually, the molecular sedimentation film is distinguished from a thin film (molecule build-up film) formed by LB process in viewpoints of differences in a agglomeration structure and in a higher-order structure or functional differences caused by the structure.

As disclosed in Japanese Patent Application Laid-Open No. Showa 57(1982)-51781, the organic compound layer can also be formed by dissolving a binder such as a resin and the material compounds into a solvent to prepare a solution, followed by forming a thin film from the prepared solution in accordance with the spin coating process and the like.

In the present invention, any well known light emitting material other than the anthracene derivatives of the present invention may be optionally contained in the light emitting layer; or a light emitting layer including other well known light emitting layer may be laminated with the light emitting layer containing the light emitting material of the present invention each in an extent of not obstructing to achieve the object of the present invention respectively.

Next, the hole injecting layer and the hole transporting layer are layers which assist injection of holes into the light emitting layer and transport the holes to the light emitting zone. The layers exhibit a great mobility of holes and, in general, have an ionization energy as small as 5.5 eV or smaller. For the hole injecting layer and the hole transporting layer, a material which transports holes to the light emitting layer at a small strength of the electric field is preferable. A material which exhibits, for example, a mobility of holes of at least $10^{-4}$ cm$^2$/V·sec under application of an electric field of from $10^4$ to $10^6$ V/cm is preferable. As for such material, any arbitrary material selected from conventional material commonly used as a charge transporting material for the holes in photoconduction materials and well known material employed for the hole injecting layer in the EL device is employable.

Specific examples include triazole derivatives (refer to U.S. Pat. No. 3,112,197, etc.), oxadiazole derivatives (refer to U.S. Pat. No. 3,189,447, etc.), imidazole derivatives (refer to Japanese Examined Patent KOKOKU No. Shou 37-16096, etc.), poly arylalkane derivatives (refer to U.S. Pat. Nos. 3,615,402, 3,820,989 and 3,542,544, Japanese Examined Patent KOKOKU Nos. Shou 45-555 and Shou 51-10983, Japanese Unexamined Patent Application Laid-Open Nos. Shou 51-93224, Shou 55-17105, Shou 56-4148, Shou 55-108667, Shou 55-156953, Shou 56-36656, etc.), pyrazoline derivatives and pyrazolone derivatives (refer to U.S. Pat. Nos. 3,180,729 and 4,278,746, Japanese Unexamined Application Patent Laid-Open Nos. Shou 55-88064, Shou 55-88065, Shou 49-105537, Shou 55-51086, Shou 56-80051, Shou 56-88141, Shou 57-45545, Shou 54-112637, Shou 55-74546, etc.), phenylenediamine derivatives (refer to U.S. Pat. No. 3,615,404, Japanese Examined Patent KOKOKU Nos. Shou 51-10105, Shou 46-3712 and Shou 47-25336, Japanese Unexamined Patent Application Laid-Open Nos. Shou 54-53435, Shou 54-110536, Shou 54-119925, etc.), arylamine derivatives (refer to U.S. Pat. Nos. 3,567,450, 3,180,703, 3,240,597, 3,658,520, 4,232,103, 4,175,961 and 4,012,376, Japanese Examined Patent KOKOKU Nos. Shou 49-35702 and Shou 39-27577, Japanese Unexamined Patent Application Laid-Open Nos. Shou 55-144250, Shou 56-119132 and Shou 56-22437, West German Patent No. 1,110,518, etc.), chalcone derivatives which is substituted with amino group (refer to U.S. Pat. No. 3,526,501, etc.), oxazole derivatives (disclosed in U.S. Pat. No. 3,257,203, etc.), styryl anthracene derivatives (refer to Japanese Unexamined Patent Application Laid-Open No. Shou 56-46234, etc.), fluorenone derivatives (refer to Japanese Unexamined Patent Application Laid-Open No. Shou 54-110837, etc.), hydrazone derivatives (refer to U.S. Pat. Nos. 3,717,462, Japanese Unexamined Patent Application Laid-Open Nos. Shou 54-59143, Shou 55-52063, Shou 55-52064, Shou 55-46760, Shou 55-85495, Shou 57-11350, Shou 57-148749, Hei 2-311591, etc.), stilbene derivatives (refer to Japanese Unexamined Patent Application Laid-Open Nos. Shou 61-210363, Shou 61-228451, Shou 61-14642, Shou 61-72255, Shou 62-47646, Shou 62-36674, Shou 62-10652, Shou 62-30255, Shou 60-93455, Shou 60-94462, Shou 60-174749, Shou 60-175052, etc.), silazane derivatives (U.S. Pat. No. 4,950,950), polysilane-based copolymers (Japanese Unexamined Patent Application Laid-Open No. Hei 2-204996), aniline-based copolymers (Japanese Unexamined Patent Application Laid-Open No. Hei 2-282263), an electroconductive polymer oligomer which is disclosed in Japanese Unexamined Patent Application Laid-Open No Hei 1-211399 (particularly, thiophene oligomer), etc.

With regard to the material of the hole injecting layer, the above materials are also employable, however, porphyrin compounds, aromatic tertiary amine compounds and styryl amine compounds (refer to U.S. Pat. No. 4,127,412, Japanese Unexamined Patent Application Laid-Open Nos. Shou 53-27033, Shou 54-58445, Shou 54-149634, Shou 54-64299, Shou 55-79450, Shou 55-144250, Shou 56-119132, Shou 61-295558, Shou 61-98353, Shou 63-295695, etc.) are preferable and the aromatic tertiary amine compounds are particularly preferable.

Further examples include, for example, 4,4'-bis (N-(1-naphthyl)-N-phenylamino) biphenyl (abbreviated as NPD hereunder) having 2 fused aromatic rings in its molecular described in U.S. Pat. Nos. 5,061,569, 4,4',4"-tris (N-(3-methylphenyl)-N-phenylamino)triphenyl amine (abbreviated as MTDATA hereunder) made by connecting three triphenyl amine units to form a star burst type, etc.

Further, besides the above-mentioned anthracene derivative described as a material for the light emitting layer, inorganic compound such as p-type silicon, p-type silicon carbide or so is employable as the material for the hole injecting layer.

To form the hole injecting layer or the hole transporting layer, a thin film may be formed from the material for the hole injecting layer or the hole transporting layer, respectively, in accordance with a well known process such as the vacuum vapor deposition process, the spin coating process, the casting process and the LB process. Although the thickness of the hole injecting layer and the hole transporting layer is not particularly limited, the thickness is usually from 5 nm to 5 µm.

In the organic EL device of the present invention, the organic semiconductor layer assists to inject the holes or to inject the electrons into the light emitting layer, and it is preferable for the organic semiconductor layer to have a electric conductivity of $10^{-10}$ S/cm or greater. With regard to a material for the organic semiconductor layer, electroconductive oligomers such as an oligomer having thiophene, an oligomer having arylamine disclosed in Japanese Unexamined Patent Application Laid-Open No. 8-193191 and so on, electroconductive dendrimers such as a dendrimer having an arylamine dendrimer and so on are employable.

The electron injection layer in the organic EL device of the present invention is a layer which assists injection of electrons into the light emitting layer and exhibits a great mobility of electrons. Among the electron injecting layers, an adhesion improving layer is a layer made of a material exhibiting excellent adhesion with the cathode.

Further, it is known that because the emitted light reflects on the electrode (in the above case, on the cathode) in the organic EL device, the light taken out directly through the anode and the light taken out from the electrode (cathode) via reflection interfere each other. In order for utilizing the interference effect effectively, the electron transporting layer is appropriately selected to be several nm to several µm in thickness. However, when the film thickness is thick, a material which exhibits, for example, a mobility of electrons at least $10^{-5}$ cm$^2$/Vs under application of an electric field of from $10^4$ to $10^6$ V/cm is preferable for the purpose of evading an elevation of driving electric voltage.

As the material for the electron injecting layer, 8-hydroxyquinoline, metal complexes of derivatives thereof and oxadiazole derivatives are preferable. Examples of the 8-hydroxyquinoline and metal complexes of derivatives thereof include metal chelates of oxinoid compounds including chelates of oxine (in general, 8-quinolinol or 8-hydroxyquinoline). For example, tris(8-quinolinol)aluminum (Alq) can be employed as the electron injecting material.

pyrenyl group. Further, examples of the arylene group include a phenylene group, a naphthylene group, a biphenylene group, an anthranylene group, a perilenylene group, a pyrenylene group, etc. Furthermore, examples of the substituent include an alkyl group having 1 to 10 carbon atoms, an alkoxy group or a cyano group each having 1 to 10 carbon atoms respectively, etc. With regard to the electron transfer compound, those compounds having a thin film forming capability are preferable.

Specific examples of the electron transfer compounds are shown below:

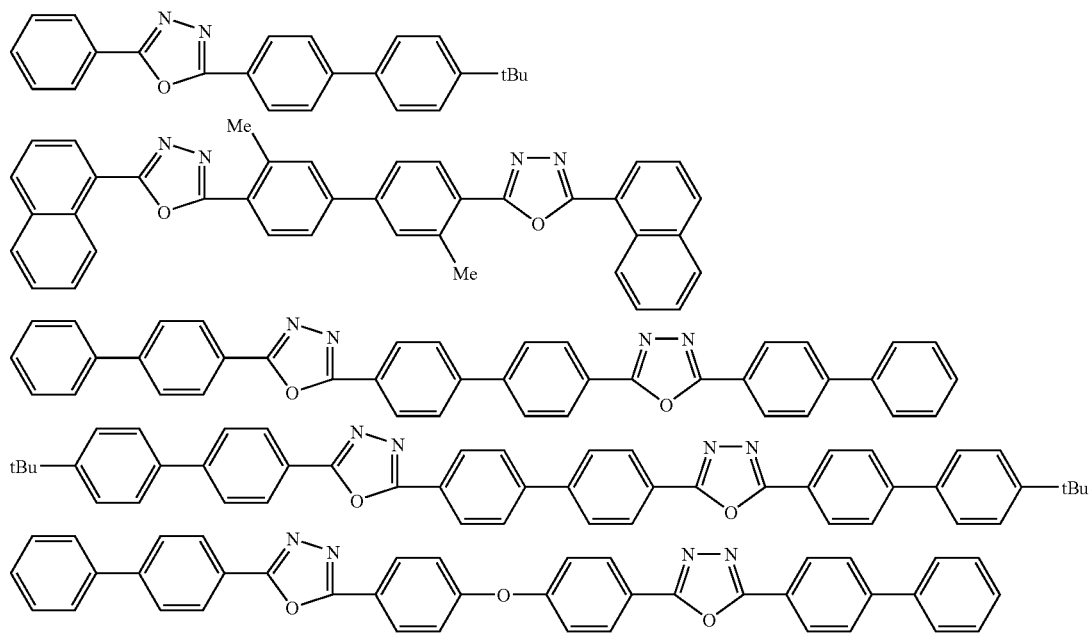

Further, examples of the oxadiazole deliveries include an electron transfer compound shown as the following general formulae:

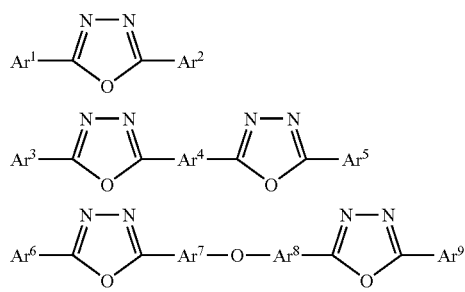

wherein Ar$^1$, Ar$^2$, Ar$^3$, Ar$^5$, Ar$^6$ and Ar$^9$ each independently represents a substituted or unsubstituted aryl group respectively, which may be the same with or different from each other; Ar$^4$, Ar$^7$ and Ar$^8$ each independently represents a substituted or unsubstituted arylene group, which may be the same with or different from each other.

Examples of the aryl group include a phenyl group, a biphenyl group, an anthranil group, a perilenyl group and a Further, materials shown by following general formulae (A) to (G) are employable for the electron injecting layer and the electron transporting layer.

A heterocyclic derivative having a nitrogen atom represented by a following general formula (A) or general formula (B):

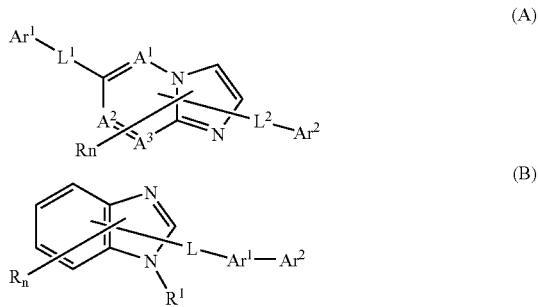

In the general formulae (A) and (B), A$^1$ to A$^3$ each independently represents a nitrogen atom or a carbon atom.

Ar$^1$ represents a substituted or unsubstituted aryl group having 6 to 60 ring carbon atoms or a substituted or unsubstituted heteroaryl group having 3 to 60 ring carbon atoms; Ar$^2$ represents a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, a substituted or unsubstituted alkoxy group having 1 to 20 carbon atoms or those divalent groups. However, at least one of $Ar^1$ or $Ar^2$ represents a substituted or unsubstituted condensed ring group having 1 to 50 ring carbon atoms or a substituted or unsubstituted mono-hetero condensed ring group having 3 to 60 ring carbon atoms.

$L^1$, $L^2$ and L each independently represents a single bond, a substituted or unsubstituted arylene group having 6 to 60 ring carbon atoms, a substituted or unsubstituted heteroarylene group having 6 to 60 ring carbon atoms or a substituted or unsubstituted fluorenylene group.

R represents a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, or a substituted or unsubstituted alkoxy group having 1 to 20 carbon atoms; n represents an integer of 0 to 5; when n is 2 or greater, plural of R may be the same with or different from each other; and adjacent couple of the plural of R may bond to form a carbocyclic aliphatic ring or a carbocyclic aromatic ring.

A heterocyclic derivative having a nitrogen atom represented by a following general formula (C):

$$HAr-L-Ar^1—Ar^2 \quad (C)$$

wherein HAr represents a heterocyclic group having nitrogen atom with 3 to 40 carbon atoms and further may have a substituent; L represents a single bond, a substituted or unsubstituted arylene group having 6 to 60 ring carbon atoms, a substituted or unsubstituted heteroarylene group having 6 to 60 ring carbon atoms or a substituted or unsubstituted fluorenylene group; $Ar^1$ represents a divalent aromatic hydrocarbon group having 6 to 60 carbon atoms and further may have a substituent; and $Ar^2$ represents a substituted or unsubstituted aryl group having 6 to 60 ring carbon atoms, a substituted or unsubstituted heteroaryl group having 3 to 60 ring carbon atoms.

A silacyclopentadiene derivative represented by a following general formula (D):

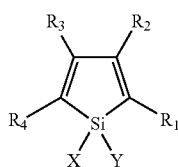

(D)

In the general formula (D), X and Y each independently represents a saturated or unsaturated hydorocarbon group having 1 to 6 carbon atoms, an alkoxy group, an alkenyloxy group, an alkynyl oxy group, a hydroxy group, a substituted or unsubstituted aryl group, a substituted or unsubstituted hetero ring, or a structure forming a saturated or unsaturated ring by bonding X and Y; $R_1$ to $R_4$ each independently represents a hydrogen atom, a halogen atom, a substituted or unsubstituted alkyl group having 1 to 6 carbon atoms, an alkoxy group, an aryloxy group, a perfluoroalkyl group, a perfluoro alkoxy group, an amino group, an alkyl carbonyl group, an arylcarbonyl group, an alkoxycarbonyl group, an aryloxycarbonyl group, an azo group, an alkylcarbonyl oxy group, an arylcarbonyl oxy group, carbalkoxy oxy group, aryloxy carbonyl oxy group, a sulfinyl group, a sulfonyl group, a sulfanilic group, a silyl group, a carbamoyl group, an aryl group, a hetero ring group, an alkenyl group, an alkynyl group, a nitro group, a formyl group, a nitroso group, a formyloxy group, an isocyano group, a cyanate group, an isocyanate group, a thiocyanate group, an isothiocyanate group or a cyano group; or in an adjacent case, a structure made by condensing a substituted or unsubstituted ring.

A borane derivative represented by a following general formula (E):

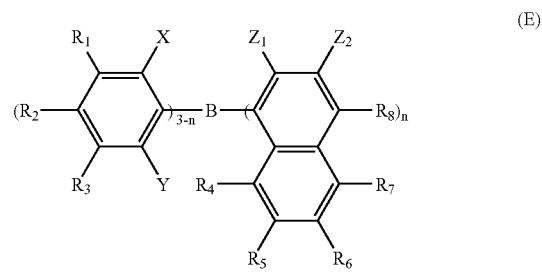

(E)

In the general formula (E), $R_1$ to $R_8$ and $Z_2$ each independently represents a hydrogen atom, a halogen atom, a saturated or unsaturated hydrocarbon group, an aromatic group, a hetero ring group, substituted amino group, a substituted boryl group, an alkoxy group or an aryloxy group; X, Y and $Z_1$ each independently represents a saturated or unsaturated hydrocarbon group, an aromatic group, a hetero ring group, substituted amino group, an alkoxy group or an aryloxy group; substituent of $Z_1$ and $Z_2$ may bonds each other to form a condensed ring; n represents an integer of 1 to 3, and when n is 2 or grater, plural of $Z_1$ may be different from each other. However, a case where n is 1, where X, Y and $R_2$ are methyl groups, and where $R_8$ is a hydrogen atom or a substituted boryl group and a case where n is 3 and where $Z_1$ is a methyl group are excluded.

(F)

In the general formula (F), $Q_1$ and $Q_2$ each independently represents a ligand expressed by a following general formula (G), L represents a halogen atom, a saturated or unsaturated alkyl group, a saturated or unsaturated cycloalkyl group, a saturated or unsaturated aryl group, a saturated or unsaturated heterocyclic group, and —$OR^1$ ($R^1$ represents a saturated or unsaturated cycloalkyl group, a saturated or unsaturated aryl group, a saturated or unsaturated heterocyclic group) or a ligand expressed by —O—Ga-$Q^3(Q^4)$, wherein $Q^3$ and $Q^4$ are the same as $Q_1$ and $Q_2$.

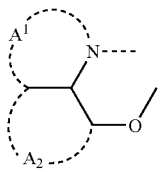

(G)

wherein rings $A^1$ and $A^2$ each represents a condensed 6-member aryl ring structure which may be substituted.

The metal-complex is powerfully characterized as n type semiconductor, and its electron injection capability is exciting. Besides, because generation energy in complex formation is small, bonding property between the metal in the formed metal-complex and the ligand becomes strong, and as a result, fluorescence quantum efficiency as the light emitting material also becomes great.

Specific examples of substituent of rings $A^1$ and $A^2$ each forming the ligand of general formula (G) include halogen atoms such as chlorine atom, bromine atom, iodine atom and fluorine atom; substituted or unsubstituted alkyl group such as methyl group, ethyl group, propyl group, butyl group, sec-butyl group, tert-butyl group, pentyl group, hexyl group, heptyl group, octyl group, stearyl group, trichloromethyl group, etc.; substituted or unsubstituted aryl group such as phenyl group, naphthyl group, 3-methylphenyl group, 3-methoxyphenyl group, 3-fluorophenyl group, 3-trichloromethylphenyl group, 3-trifluoromethylphenyl group, 3-nitrophenyl group, etc.; substituted or unsubstituted alkoxy group such as methoxy group, n-butoxy group, tert-butoxy group, trichloromethoxy group, trifluoroethoxy group, pentafluoropropoxy group, 2,2,3,3-tetrafluoropropoxy group, 1,1,1,3,3,3-hexafluoro-2-propoxy group, 6-(perfluoroethyl) hexyloxy group, etc.; substituted or unsubstituted aryloxy group such as phenoxy group, p-nitrophenoxy group, p-tert-butylphenoxy group, 3-fluorophenoxy group, pentafluorophenyl group, 3-trifluoromethylphenoxy group, etc.; substituted or unsubstituted alkylthio group such as methylthio group, ethylthio group, tert-butylthio group, hexylthio group, octylthio group, trifluoromethylthio group, etc.; substituted or unsubstituted arylthio group such as phenylthio group, p-nitrophenylthio group, p-tert-butylphenylthio group, 3-fluorophenylthio group, pentafluorophenylthio group, 3-trifiluoromethylphenylthio group, etc.; mono- or di-substituted amino group such as cyano group, nitro group, amino group, methylamino group, diethylamino group, ethylamino group, diethylamino group, dipropylamino group, dibutyl amino group, diphenylamino group, etc.; acylamino-group such as bis(acetoxymethyl)amino group, bis(acetoxyethyl) amino group, bis(acetoxypropyl)amino group, bis(acetoxybutyl) amino group, etc.; carbamoyl group such as hydroxy group, siloxy group, acyl group, methylcarbamoyl group, dimethylcarbamoyl group, ethylcarbamoyl group, diethylcarbamoyl group, a propylcarbamoyl goup, butyl carbamoyl group, a phenylcarbamoyl group, etc.; cycloalkyl group such as carboxylic acid group, sulfonic acid group, imido group, cyclopentane group, cyclohexyl group, etc.; aryl group such as phenyl group, naphthyl group, biphenyl group, anthranil group, phenanthryl group, fluorenyl group, pyrenyl group, etc.; heterocyclic group such as pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morpholidinyl group, piperazinyl group, triazinyl group, carbazolyl group, furanyl group, thiophenyl group, oxazolyl group, an oxadiazolyl group, a benzoxazolyl group, a thiazolyl group, a thiadiazolyl group, benzothiazolyl group, triazolyl group, imidazolyl group, benzimidazolyl group, pranyl group, etc. Further, above-mentioned substituents may bond each other to form further 6-member aryl ring or heterocycle.

In the present invention, it is preferable that a reductive dopant is added in either the electron transporting zone or an interfacial zone between the cathode and the organic layer. The reductive dopant used in the present invention is defined as a substance which reduces the electron transporting compound. Examples of the reductive dopant include at least one compound selected from alkali metals, alkali metallic complexes, alkali metal compounds, alkaline earth metals, alkaline earth metallic complexes, alkaline earth metal compounds, rare earth metals, rare earth metallic complexes and rare earth metal compounds. Examples of the alkali metal compound, the alkaline earth metal compound and the rare earth metal compound described above include oxides and halides of the respective metals.

Specific examples of the preferable reductive dopant include at least one alkali metal selected from a group consisting of Li (the work function: 2.93 ev), Na (the work function: 2.36 eV), K (the work function: 2.28 eV), Rb (the work function: 2.16 eV) and Cs (the work function: 1.95 eV) or at least one alkaline earth metals selected from a group consisting of Ca (the work function: 2.9 eV), Sr (the work function: 2.0 to 2.5 eV) and Ba (the work function: 2.52 eV); whose work function of 2.9 eV or smaller is particularly preferable. Among those, more preferable reductive dopants include at least one kind or more alkali metal selected from the group consisting of K, Rb and Cs, the latter Rb or Cs being farther more preferable and the last Cs being the most preferable. Those alkali metals have particularly high reducing capability, and only an addition of relatively small amount of them into an electron injection zone enables to achieve both improvement of luminance and lifetime extension of the organic EL device. Further, with regard to the reductive dopant with work function of 2.9 eV or smaller, a combination of two or more kinds of the alkali metal is also preferable, and particularly, combinations containing Cs, for example, combinations of Cs and Na, Cs and K, Cs and Rb, or Cs and Na and K are preferable. Containing Cs in combination enables to reveal reducing capability effectively, and the addition into the electron injection zone expects both improvement of luminance and lifetime extension of the organic EL device.

In the organic EL device of the present invention, an electron injecting layer formed with an insulating material or a semiconductor may be further sandwiched between the cathode and the organic thin film layer. The electron injecting layer effectively prevents leak in the electric current and improves the electron injecting capability. It is preferable that at least one metal compound selected from the group consisting of alkali metal chalcogenides, alkaline earth metal chalcogenides, alkali metal halides and alkaline earth metal halides is used as the insulating material. It is preferable that the electron injecting layer is constituted with the above alkali metal chalcogenide since the electron injecting property can be improved. Preferable examples of the alkali metal chalcogenide include $Li_2O$, LiO, $Na_2S$, $Na_2Se$ and NaO. Preferable examples of the alkaline earth metal chalcogenide include CaO, BaO, SrO, BeO, BaS and CaSe. Preferable examples of the alkali metal halide include LiF, NaF, KF, LiCl, KCl and NaCl. Preferable examples of the alkaline earth metal halide include fluorides such as $CaF_2$, $BaF_2$, $SrF_2$, $MgF_2$ and $BeF_2$ and halides other than the fluorides.

Examples of the semiconductor constituting the electron transporting layer include oxides, nitrides and nitriding oxides containing at least one element selected from Ba, Ca, Sr, Yb, Al, Ga, In, Li, Na, Cd, Mg, Si, Ta, Sb and Zn, which are used singly or in combination of two or more. It is preferable that the inorganic compound constituting the electron transporting layer is in the form of a fine crystalline or amorphous insulating thin film. When the electron transporting layer is constituted with the above insulating thin film, a more uniform thin film can be formed and defective pixels such as dark spots can be decreased. Examples of the inorganic compound include the alkali metal chalcogenides, the alkaline earth metal chalcogenides, the alkali metal halides and the alkaline earth metal halides which are described above.

As the cathode for the organic EL device of the present invention, an electrode substance such as metal, alloy, electro conductive compound and those mixture having a small work function (4 eV or smaller) is employed. Examples of the electrode substance include potassium, sodium-potassium alloy, magnesium, lithium, magnesium-silver alloy, aluminum/aluminum oxide, aluminum-lithium alloy, indium, rare earth metal, etc. The cathode can be prepared by forming a thin film of the electrode material described above in accordance with a process such as the vapor deposition process and the sputtering process.

When the light emitted from the light emitting layer is observed through the cathode, it is preferable that the cathode has a transmittance of the emitted light greater than 10%. It is also preferable that the sheet resistivity of the cathode is several hundred $\Omega/\square$ or smaller. The thickness of the cathode is, in general, selected in the range of from 10 nm to 1 μm and preferably in the range of from 50 to 200 nm.

In general, an organic EL device tends to form defects in pixels due to leak and short circuit since an electric field is applied to ultra-thin films. To prevent the formation of the defects, a layer of an insulating thin film may be inserted between the pair of electrodes.

Examples of the material employed for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide. Mixtures and laminates of the above compounds can also be employed.

To fabricate an organic EL device of the present invention, for example, an anode, a light emitting layer and, where necessary, a hole injecting layer and an electron injecting layer are formed in accordance with the aforementioned process using the aforementioned materials, and a cathode is formed in the last step. An organic EL device may be produced by forming the aforementioned layers in the order reverse to that described above, i.e., a cathode being formed in the first step and an anode in the last step.

An embodiment of the process for producing an organic EL device having a construction in which an anode/a hole injecting layer/a light emitting layer/an electron injecting layer/a cathode are disposed sequentially on a light-transmitting substrate will be described in the following.

On a suitable light-transmitting substrate, a thin film made of a material for the anode is formed in accordance with the vapor deposition process or the sputtering process so that the thickness of the formed thin film is 1 μm or smaller and preferably in the range of 10 to 200 nm. The formed thin film is employed as the anode. Then, a hole injecting layer is formed on the anode. The hole injecting layer can be formed in accordance with the vacuum vapor deposition process, the spin coating process, the casting process or the LB process, as described above. The vacuum vapor deposition process is preferable since a uniform film can be easily obtained and the possibility of formation of pin holes is small. When the hole injecting layer is formed in accordance with the vacuum vapor deposition process, in general, it is preferable that the conditions in general are suitably selected in the following ranges: temperature of the deposition source: 50 to 450° C.; vacuum level: $10^{-7}$ to $10^{-3}$ torr; deposition rate: 0.01 to 50 nm/second; temperature of the substrate: −50 to 300° C.; and film thickness: 5 nm to 5 μm; although the conditions of the vacuum vapor deposition are different depending on the employed compound (the material for the hole injecting layer) and the crystal structure and the recombination structure of the hole injecting layer to be formed.

Subsequently, the light-emitting layer is formed on the hole-injecting layer formed above. Also the formation of the light emitting layer can be made by forming the light emitting material according to the present invention into a thin film in accordance with the vacuum vapor deposition process, the sputtering process, the spin coating process or the casting process. The vacuum vapor deposition process is preferable because a uniform film can be easily obtained and the possibility of formation of pinholes is small. When the light-emitting layer is formed in accordance with the vacuum vapor deposition process, in general, the conditions of the vacuum vapor deposition process can be selected in the same ranges as those described for the vacuum vapor deposition of the hole-injecting layer although the conditions are different depending on the used compound. It is preferable that the thickness is in the range of from 10 to 40 nm.

Next, the electron-injecting layer is formed on the light-emitting layer formed above. Similarly to the hole injecting layer and the light-emitting layer, it is preferable that the electron-injecting layer is formed in accordance with the vacuum vapor deposition process since a uniform film must be obtained. The conditions of the vacuum vapor deposition can be selected in the same ranges as those for the hole injecting layer and the light-emitting layer.

In the last step, the cathode is formed on the electron-injecting layer, and an organic EL device can be fabricated. The anode is made of a metal and can be formed in accordance with the vacuum vapor deposition process or the sputtering process. It is preferable that the vacuum vapor deposition process is employed in order to prevent the lower organic layers from damages during the formation of the film.

In the above fabrication of the organic EL device, it is preferable that the above layers from the anode to the cathode are formed successively while the production system is kept in a vacuum after being evacuated.

The process for forming the layers in the organic EL device of the present invention is not particularly limited. A conventional process such as the vacuum vapor deposition process and the spin coating process can be used. The organic thin film layer comprising the compound represented by the foregoing general formula (1) used in the organic EL device of the present invention can be formed in accordance with the vacuum vapor deposition process, the molecular beam epitaxy process (the MBE process) or, using a solution prepared by dissolving the compound into a solvent, in accordance with a conventional coating process such as the dipping process, the spin coating process, the casting process, the bar coating process and the roller coating process.

The thickness of each layer in the organic thin film layer in the organic EL device of the present invention is not particularly limited. In general, an excessively thin layer tends to have defects such as pin holes, and an excessively thick layer requires a high applied voltage results in decreasing the efficiency. Therefore, a thickness within the range of several nanometers to 1 μm is preferable.

The organic EL device which can be produced as described above emits light when a direct voltage of 5 to 40 V is applied in the condition that the anode is connected to a positive electrode (+) and the cathode is connected to a negative electrode (−). When the connection is reversed, no electric current is observed and no light is emitted at all. When an alternating voltage is applied to the organic EL device, the uniform light emission is observed only in the condition that the polarity of the anode is positive and the polarity of the cathode is negative. When an alternating voltage is applied to the organic EL device, any type of wave shape can be employed.

EXAMPES

The present invention will be explained in detail with Examples below.

Synthesis Example 1

Synthesis of Compound AN-1

Commercially available 5-bromo acenaphthene in an amount of 5.0 g and 10-(4-naphthalene-1-yl-phenyl) anthracene-9-boronic acid synthesized by well known method in an amount of 9.5 g were dissolved into a mixed solution of 80 milliliter of dimethoxyethane (DME) and 30 milliliter of toluene. Further adding tetrakis triphenylphosphine palladium in an amount of 0.98 g and 2M-sodium carbonate aqueous solution in an amount of 40 milliliter, an atmospheric air was replaced with argon gas. The resultant solution was refluxed under heating for 9.5 hours, cooled by leaving it standing and precipitated crystals were separated by filtration. The resultant crystals were washed with the use of water and methanol, and after refining them by means of silicagel column chromatography (spreading solvent: hexane/toluene=2/1), 6.2 g of the aimed Compound (AN-1) as pale yellow crystals were obtained (yield: 54%).

The pale yellow crystals were identified as the aimed Compound (AN-1) from the result that m/z=532 for $C_{42}H_{28}$=532 in accordance with Field Desorption Mass Spectrum (FD-MS) measurement and from $^1$H-NMR spectrum. $^1$H-nmr (500 MHz, $CDCl_3$, ppm): δ 3.53 (s, 4H), 7.34-8.14 (m, 24H)

Synthesis Example 2

Synthesis of Compound AN-2

(1) Synthesis of Intermediate Product 5-(4-bromophenyl) acenaphthene

Commercially available 5-bromo acenaphthene in an amount of 11.7 g was dissolved into a mixed solution of dehydrated toluene in an amount 50 milliliter and dehydrated ether in an amount of 50 milliliter, and the resultant solution was cooled down to −40° C. under an atmosphere of argon gas. Thirty five milliliter of 1.6M-normal butyllithium hexane solution was dripped into the resultant solution, followed by elevating the temperature up to −10° C. Two hours later, the resultant solution was cooled down to −70° C. and further, another solution prepared by dissolving triisopropoxyborane in an amount of 35 milliliter into 50 milliliter of ether was dripped into the solution. After stirring the resultant solution for 3 hours at the temperature of −70° C., it was left standing for one night. After the night, the resultant solution was acidified in a dilute hydrochloric acid of 10% by weight and an organic layer was extracted with the use of toluene. Washing with the use of both dilute hydrochloric acid and a saturated sodium chloride solution, the organic layer was dried with anhydrous sodium sulfate, and the organic solvent was distillated by means of an evaporator. Crystallizing the residues with the use of toluene/hexane, 4.5 g of 5-acenaphthene boronic acid was obtained (yield: 45%).

Five point nine gram of the 5-acenaphthene boronic acid obtained and 10.2 gram of 4-bromo iodobenzene were dissolved into 100 milliliter of toluene. Further adding tetrakistriphenylphosphinepalladium in an amount of 1.7 g and 2M-sodium carbonate aqueous solution in an amount of 45 milliliter, an atmospheric air was replaced with argon gas. The resultant solution was refluxed under heating for 6 hours, cooled by leaving it standing and the organic layer was extracted with the use of toluene. Washing with the use of a saturated sodium chloride solution, the organic layer was dried with anhydrous sodium sulfate, and the organic solvent was distillated by means of an evaporator. After refining the residues by means of silicagel column chromatography (spreading solvent: hexane), 9.2 g of the aimed intermediate product 5-(4-bromophenyl) acenaphthene as a pale yellow solid was obtained (yield: 100%).

(2) Synthesis of Compound AN-2

Eight point four gram of 10-(naphthalene-2-yl)anthracene-9-boronic acid synthesized in accordance with a well known process and 6.2 gram of the intermediate product 5-(4-bromophenyl)acenaphthene were dissolved into 60 milliliter of DME. Further adding tetrakistriphenylphosphinepalladium in an amount of 1.2 g and 2M-sodium carbonate aqueous solution in an amount of 30 milliliter, an atmospheric air was replaced with argon gas. The resultant solution was refluxed under heating for 8 hours, cooled by leaving it standing and precipitated crystals were separated by filtration. The resultant crystals were washed with the use of water and methanol, and after refining them by means of silicagel column chromatography (spreading solvent: toluene), 6.9 g of the aimed Compound (AN-2) as pale yellow crystals were obtained (yield: 65%).

The pale yellow crystals were identified as the aimed Compound (AN-2) from the result that m/z=532 for $C_{42}H_{28}$=532 in accordance with FD-MS measurement and from $^1$H-NMR spectrum.

1H-nmr (500 MHz, $CDCl_3$, ppm): δ 3.60 (s, 4H), 6.91-8.25 (m, 24H)

Synthesis Examples 3 to 39

Synthesis of Compounds AN-3 to AN-39

Compounds AN-3 to AN-39 were synthesized in similar manners as Example 1 except that boronic acid compounds described in Table 1 were used instead of 10-(4-naphthalene-1-yl-phenyl)anthracene-9-boronic acid and that halogen compounds described in Table 1 were used instead of 5-bromo acenaphthene each in their necessary amount respectively.

TABLE 1

| W | X | Y | Z |
|---|---|---|---|
| 1 | AN-1 | (9-(4-(naphthalen-1-yl)phenyl)anthracen-10-yl)boronic acid | 5-bromoacenaphthylene (dihydro) |
| 2 | AN-2 | (9-(naphthalen-2-yl)anthracen-10-yl)boronic acid | 5-(4-bromophenyl)acenaphthylene (dihydro) |
| 3 | AN-3 | (9-(4-(naphthalen-1-yl)phenyl)anthracen-10-yl)boronic acid | bromo-acenaphthylene (dihydro) |
| 4 | AN-4 | (9-(acenaphthylen-5-yl)anthracen-10-yl)boronic acid | 3-(3-bromophenyl)naphthalene |
| 5 | AN-5 | (9-(acenaphthylen-5-yl)anthracen-10-yl)boronic acid | 3-(2-bromophenyl)naphthalene |
| 6 | AN-6 | (4-(naphthalen-1-yl)phenyl)boronic acid | bromo-anthracenyl-triptycene derivative |

TABLE 1-continued
| W | X | Y | Z |
|---|---|---|---|
| 7 | AN-7 | 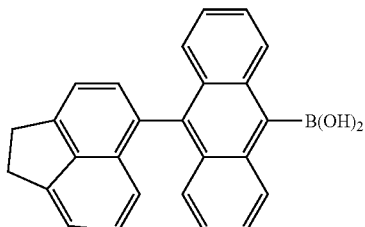 | 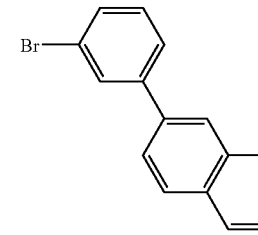 |
| 8 | AN-8 | 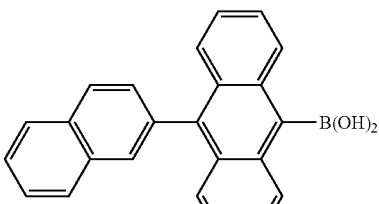 | 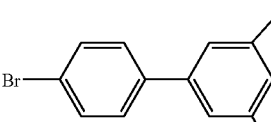 |
| 9 | AN-9 | 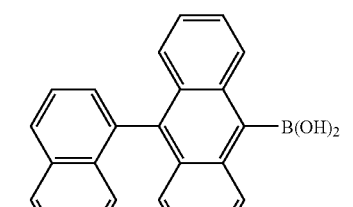 | 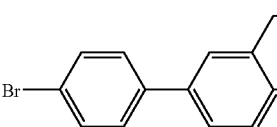 |
In the Table 1, W represents "Synthesis Example", X represents "Synthesized Compound", Y represents "Synthesis Material (Boronic acid compound)" and Z represents "Synthesis Material (Halogen compound)".
TABLE 1
(Continued)
| Synthesis Example | Synthesized Compound | Material (Boronic acid compound) | Material (Halogen compound) |
|---|---|---|---|
| 10 | AN-10 | 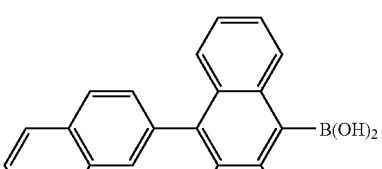 | 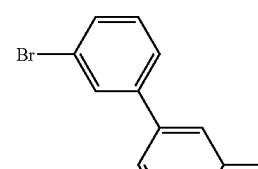 |
| 11 | AN-11 | 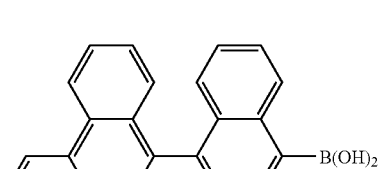 | 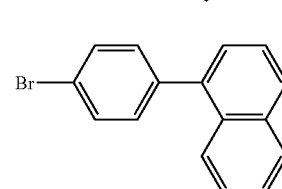 |

TABLE 1-continued (Continued)

| Synthesis Example | Synthesized Compound | Material (Boronic acid compound) | Material (Halogen compound) |
| --- | --- | --- | --- |
| 12 | AN-12 | | |
| 13 | AN-13 | | |
| 14 | AN-14 | | |
| 15 | AN-15 | | |
| 16 | AN-16 | | |
| 17 | AN-17 | | |

TABLE 1-continued
(Continued)
| Synthesis Example | Synthesized Compound | Material (Boronic acid compound) | Material (Halogen compound) |
|---|---|---|---|
| 18 | AN-18 | 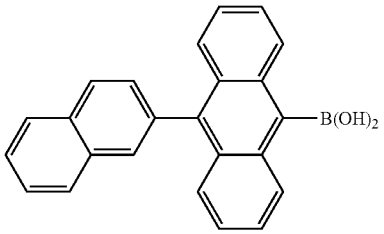 | 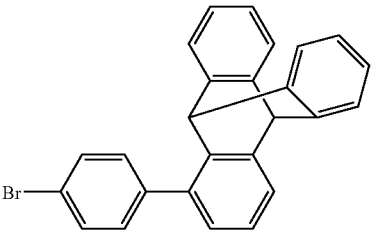 |
| 19 | AN-19 | 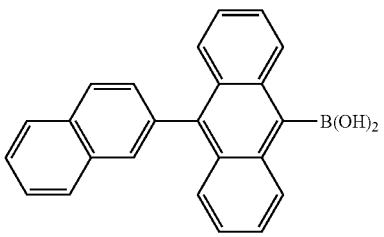 | 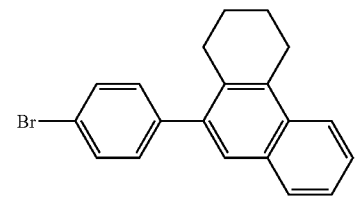 |
| 20 | AN-20 | 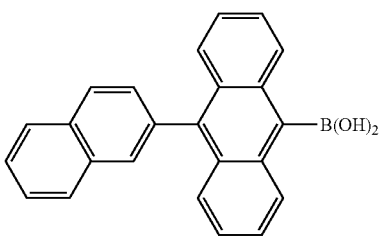 | 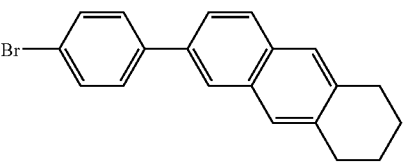 |
| 21 | AN-21 | 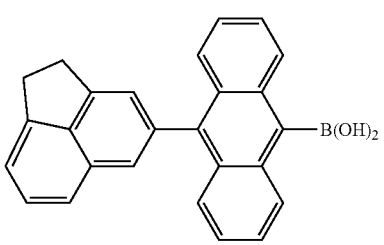 | 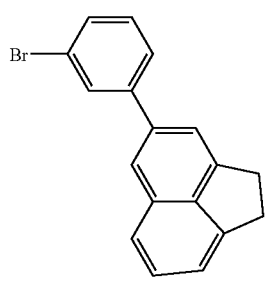 |
| 22 | AN-22 | 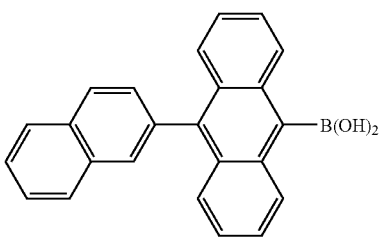 | 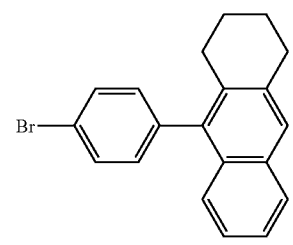 |
| 23 | AN-23 | 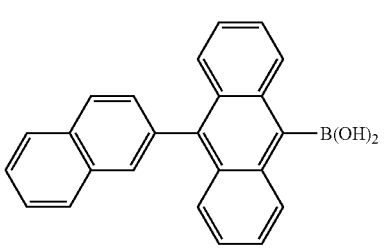 | 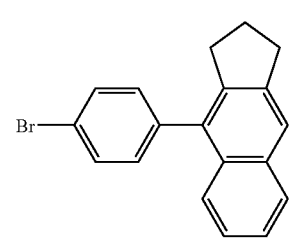 |

TABLE 1-continued (Continued)

| Synthesis Example | Synthesized Compound | Material (Boronic acid compound) | Material (Halogen compound) |
|---|---|---|---|
| 24 | AN-24 | | |
| 25 | AN-25 | | |
| 26 | AN-26 | | |
| 27 | AN-27 | | |
| 28 | AN-28 | | |

TABLE 1-continued
(Continued)
| Synthesis Example | Synthesized Compound | Material (Boronic acid compound) | Material (Halogen compound) |
|---|---|---|---|
| 29 | AN-29 | 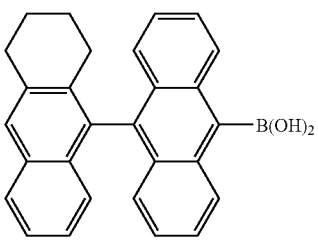 | 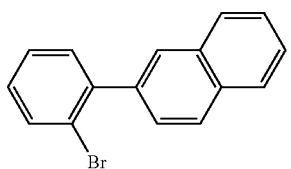 |
| 30 | AN-30 | 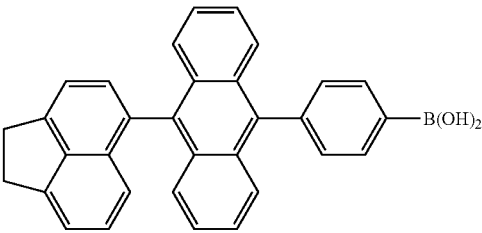 | 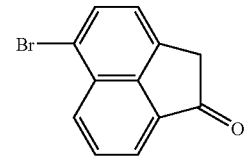 |
| 31 | AN-31 | 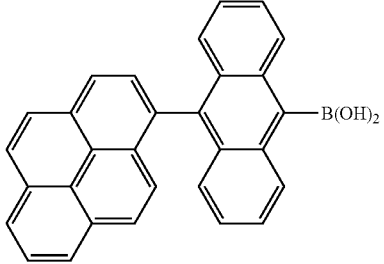 | 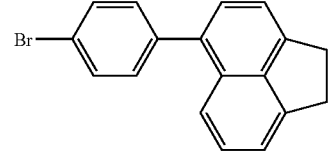 |
| 32 | AN-32 | 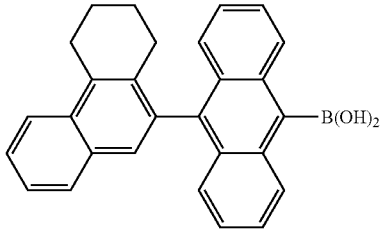 | 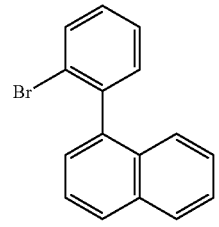 |
| 33 | AN-33 | 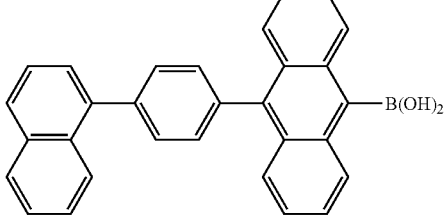 | 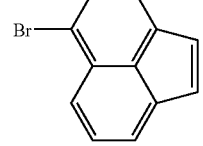 |
| 34 | AN-34 | 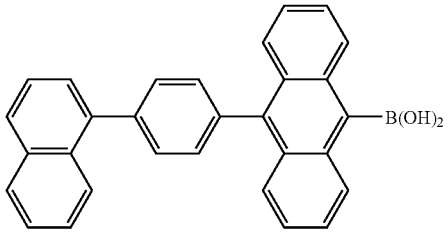 | 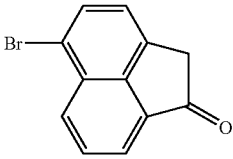 |

TABLE 1-continued

| Synthesis Example | Synthesized Compound | Material (Boronic acid compound) | Material (Halogen compound) |
|---|---|---|---|
| 35 | AN-35 | | |
| 36 | AN-36 | | |
| 37 | AN-37 | | |
| 38 | AN-38 | | |
| 39 | AN-39 | | |

Example 1

Fabrication of Organic EL Device: Example of Employing Compound AN-1

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode, a film of N,N'-bis(N,N'-diphenyl-4-aminophenyl)-N,N'-diephenyl-4,4'-diamino-1,1'-biphenyl (referred to as TPD232 film, hereinafter) having a thickness of 60 nm was formed so that the formed film covered the transparent electrode. The formed TPD232 film worked as the hole injecting layer. Successively, a film of N,N',N'-tetra(4-biphenyl)-diaminobiphenylene (referred to as TBDB film, hereinafter) having a thickness of 20 nm was formed over the TPD232 film. The formed film worked as the hole transporting layer. Further, Compound AN-1 was vapor deposited thereby forming a film having a thickness of 40 nm. At the same time, Amine Compound BD1 as a pure blue dopant below having styryl group was vapor deposited with a weight ratio of AN-1:BD1=40:3 to AN-1. The formed film worked as a light emitting layer. On the film formed above, a film of Alq having a thickness 10 nm was formed. The formed film worked as an electron injecting layer. Thereafter, Li (the source of lithium: manufactured by SAES GETTERS Company) as a reductive dopant and Alq were binary vapor deposited and an Alq:Li film (film thickness: 10 nm) was formed as the electron injecting layer (or the cathode). On the Alq:Li film, metallic aluminum was vapor deposited to form a metal cathode and an organic El device was fabricated. As a result of subjecting the fabricated organic EL device to a test by passing electric current, it was confirmed that a blue light with a luminance of 634 cd/m$^2$ was emitted at voltage of 7.85 V and a current density of 10 mA/cm$^2$. CIE chromaticities are shown in Table 2. Next, measured results of half lifetimes at initial luminance of 1000 cd/m$^2$ about the organic EL devices are shown in Table 2.

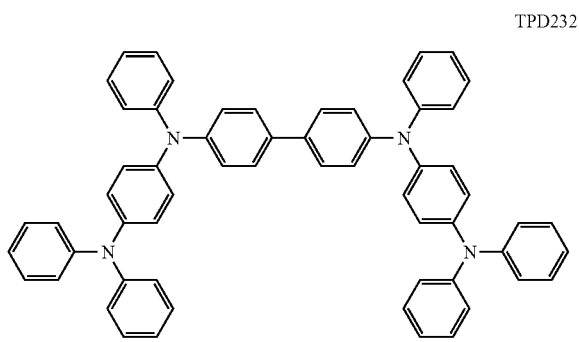

TPD232

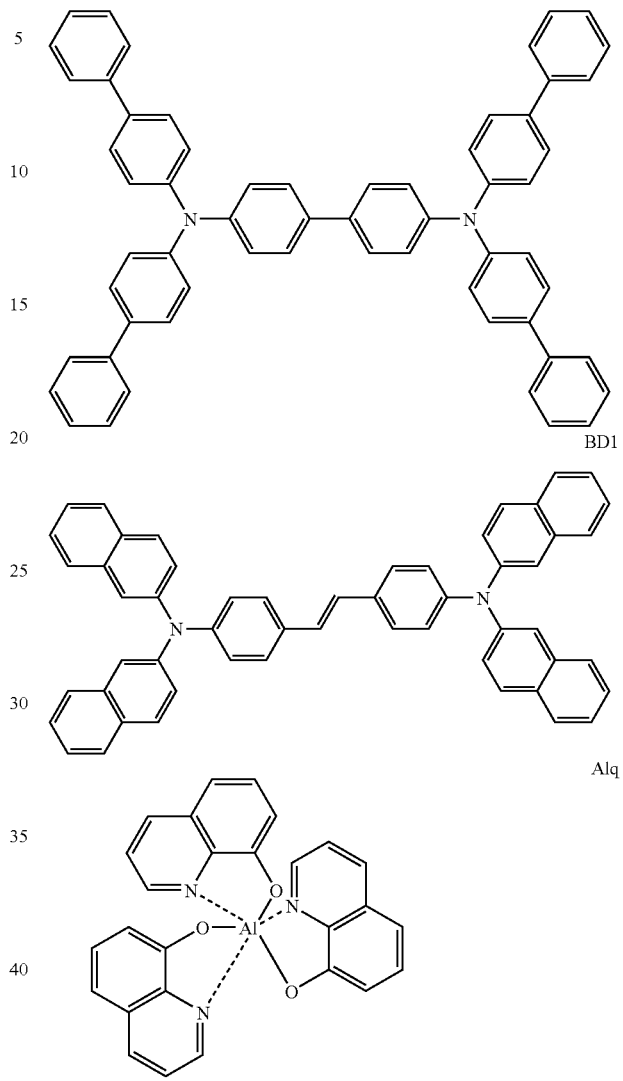

Example 2

Fabrication of Organic EL Device: Example of Employing Compound AN-2

An organic EL device was fabricated in accordance with the same procedures as those conducted in Example 1 except that Compound (AN-1) was replaced with Compound (AN-2).

Measured result of half lifetime at initial luminance of 1000 cd/m$^2$ about the organic EL devices is shown in Table 2.

Example 3

An organic EL device was fabricated in accordance with the same procedures as those conducted in Example 1 except that Amine Compound BD1 was replaced with Amine Compound BD2 below.

Measured result of half lifetime at initial luminance of 1000 cd/m$^2$ about the organic EL devices is shown in Table 2.

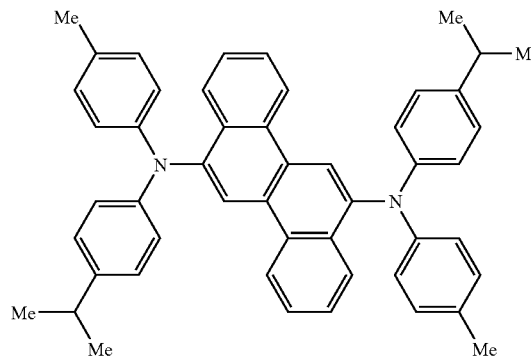

Example 4

An organic EL device was fabricated in accordance with the same procedures as those conducted in Example 1 except that Amine Compound BD1 was replaced with Amine Compound BD3 below.

Measured result of half lifetime at initial luminence of 1000 cd/m² about the organic EL devices is shown in Table 2.

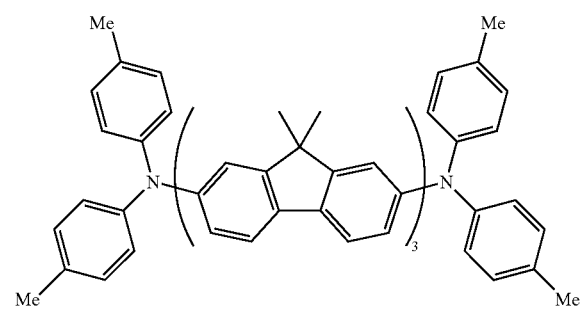

Comparative Examples 1 to 6

An organic EL devices were fabricated in accordance with the same procedures as those conducted in Example 1 except that Compound AN-1 was replaced with Compound an-1 below described in Japanese Unexamined Patent Application Laid-Open No. 2000-182776 or with Compound an-2 below described in International PCT Publication No. WO 04/018587 and except that materials for forming the light emitting layer described in Table 2 were employed.

Measured results of half lifetimes at initial luminance of 1000 cd/m² about the organic EL devices are shown in Table 2.

TABLE 2

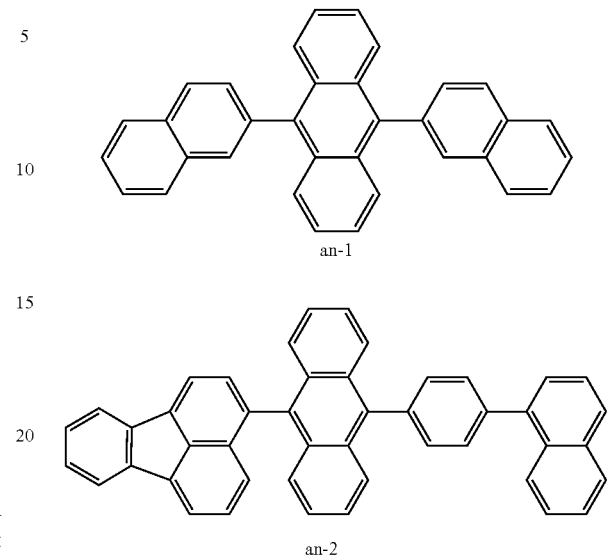

| | Forming material for Light emitting layer | Half Lifetime (hours) | Chromaticity CIEx | Chromaticity CIEy |
|---|---|---|---|---|
| Example 1 | AN-1/BD1 | 3900 | 0.15 | 0.17 |
| Example 2 | AN-2/BD1 | 4000 | 0.15 | 0.17 |
| Example 3 | AN-1/BD2 | 3500 | 0.15 | 0.15 |
| Example 4 | AN-1/BD3 | 2900 | 0.15 | 0.15 |
| Co. Example 1 | an-1/BD1 | 2000 | 0.16 | 0.19 |
| Co. Example 2 | an-2/BD1 | 3400 | 0.20 | 0.35 |
| Co. Example 3 | an-1/BD2 | 1700 | 0.15 | 0.17 |
| Co. Example 4 | an-2/BD2 | 2900 | 0.20 | 0.33 |
| Co. Example 5 | an-1/BD3 | 1400 | 0.15 | 0.16 |
| Co. Example 6 | an-2/BD3 | 2700 | 0.20 | 0.31 |

As shown in Table 2, it is verified that the Organic EL device employing the anthracene derivatives represented by the general formula (I) of the present invention has longer lifetime and higher blue purity of emitted light than Comparative Examples 1 and 2.

INDUSTRIAL APPLICABILITY

As the foregoing description in detail, the Organic EL device employing the anthracene derivatives represented by the general formula (I) of the present invention emits blue light of enhanced purity and has a long lifetime. Therefore, it is very practical as an organic EL device for color display use expective of long term continuous usage.

What is claimed is:

1. An anthracene derivative represented by general formula (I):

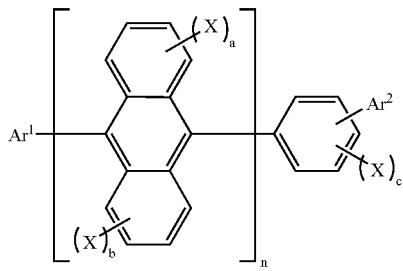

wherein

X represents a hydrogen atom, a substituted or unsubstituted aromatic group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 2 to 50 carbon atoms, a substituted or unsubstituted silyl group, a carboxyl group, a halogen atom, a cyano group, a nitro group or a hydroxyl group;

$Ar^1$ and $Ar^2$ each independently represents a substituted or unsubstituted condensed aromatic group having 10 to 50 ring carbon atoms;

at least one of $Ar^1$ or $Ar^2$ represents a a triptycenyl group represented by general formula (IV):

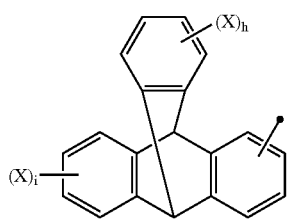

X represents the same as the foregoing description;

h and i each independently represents an integer of 0 to 4;

a, b and c each independently represents an integer of 0 to 4;

n represents an integer of a to 1 to 3; and when n is 2 or greater, within the brackets [ ], each

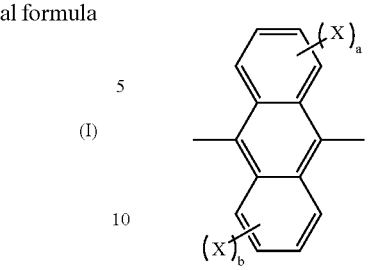

may be the same or different.

2. The anthracene derivative according to claim 1, wherein at least one of $Ar^1$ and $Ar^2$ is a 1-naphthyl group represented by general formula (II)

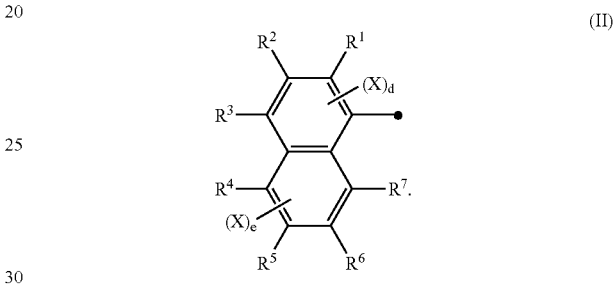

3. The anthracene derivative according to claim 1, wherein at least one of $Ar^1$ and $Ar^2$ is a 2-naphthyl group represented by general formula (III)

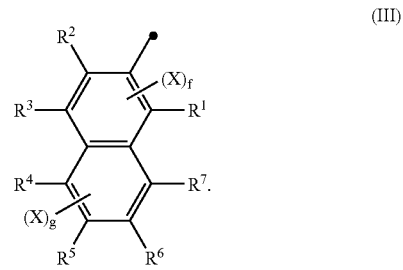

4. An organic electroluminescence device which comprising at least one organic thin film layer, wherein:

the at least one organic thin film layer comprises a light emitting layer sandwiched between a pair of electrode consisting of an anode and a cathode; and the at least one organic thin film layer comprises the anthracene derivatives according to claim 1.

5. The organic electroluminescence device according to claim 4, wherein the light emitting layer comprises an arylamine compound.

6. The organic electroluminescence device according to claim 4, wherein the light emitting layer further comprises a styrylamine compound.

7. The organic electroluminescence device according to claim 4, wherein the device emits blue light.

8. The anthracene derivative according to claim 1, Wherein at least one of $Ar^1$ and $Ar^2$ represents a group selected from the group consisting of:

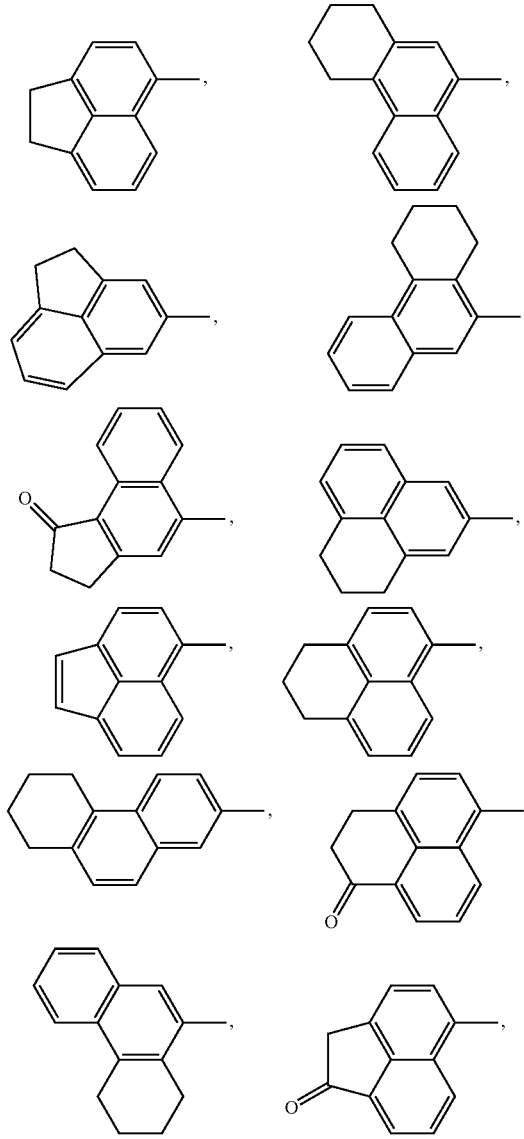
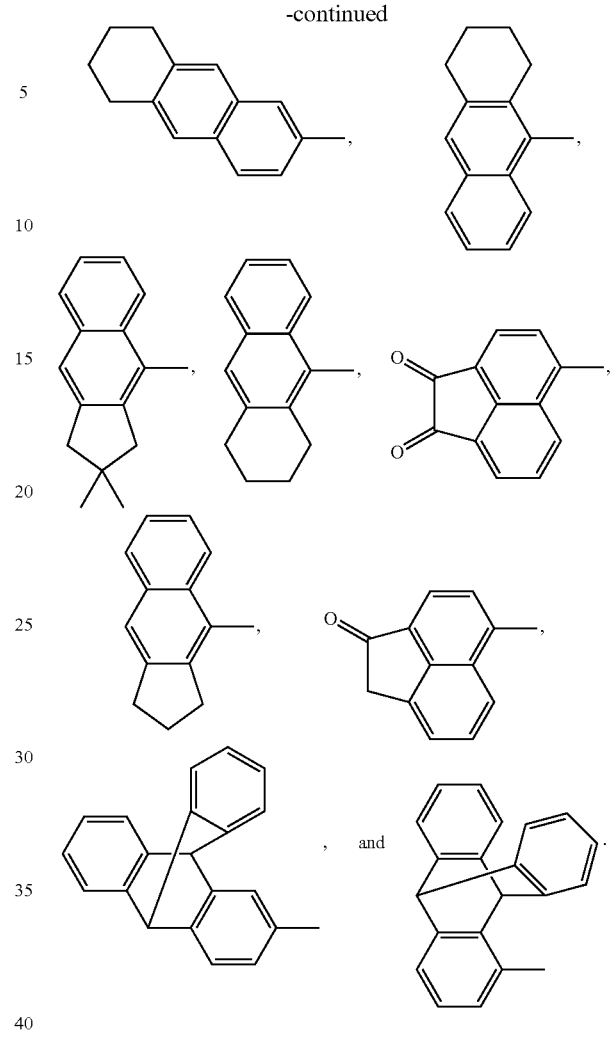
9. The organic electroluminescence device according to claim 5, wherein the device emits blue light.
10. The organic electroluminescence device according to claim 6, wherein the device emits blue light.
* * * * *